(12) United States Patent  
Young et al.

(10) Patent No.: US 8,994,743 B2  
(45) Date of Patent: Mar. 31, 2015

(54) VIRTUAL CELLULAR STAINING

(75) Inventors: Jonathan Young, Eugene, OR (US); Kathleen Free, Cheshire, OR (US); Elizabeth Browne, Eugene, OR (US)

(73) Assignee: Life Technologies Corporation, Carlsbad, CA (US)

( * ) Notice: Subject to any disclaimer, the term of this patent is extended or adjusted under 35 U.S.C. 154(b) by 352 days.

(21) Appl. No.: 13/314,001

(22) Filed: Dec. 7, 2011

(65) Prior Publication Data

US 2012/0147002 A1 Jun. 14, 2012

Related U.S. Application Data

(60) Provisional application No. 61/420,708, filed on Dec. 7, 2010, provisional application No. 61/450,519, filed on Mar. 8, 2011, provisional application No. 61/541,375, filed on Sep. 30, 2011.

(51) Int. Cl.  
*G06T 11/00* (2006.01)

(52) U.S. Cl.  
CPC .................................. *G06T 11/001* (2013.01)  
USPC ....................................................... 345/589

(58) Field of Classification Search  
CPC .......................... G06T 11/001; G06T 2210/41  
USPC ....................................................... 345/594  
See application file for complete search history.

(56) References Cited

U.S. PATENT DOCUMENTS 6,165,734 A  12/2000  Garini et al.  
7,814,163 B2 10/2010  Lee et al.  
2001/0037219 A1* 11/2001  Malik .................................. 705/2  
2005/0136549 A1  6/2005  Gholap et al.  
2007/0020697 A1  1/2007  Cualing et al.  
2007/0025504 A1*  2/2007  Tumer ............................ 378/43

(Continued)

FOREIGN PATENT DOCUMENTS

WO  WO 2010049651 A1 * 5/2010  
WO  WO-2012/078796  6/2012

OTHER PUBLICATIONS

PCT/US2011/063805 International Search Report Mailed Apr. 19, 2012, pp. 1-2.  
PCT/US2011/063805 Written Opinion Mailed Apr. 19, 2012, pp. 1-7.

(Continued)

*Primary Examiner* — Kee M Tung  
*Assistant Examiner* — Ryan D McCulley  
(74) *Attorney, Agent, or Firm* — Life Technologies Corporation

(57) ABSTRACT

Systems and methods are used to display cell structures of a biological cell. A plurality of cell structures of a biological cell is stored and for each cell structure of the plurality of cell structures one or more stain colors are stored. A selected cell structure is received from an input device. One or more stain colors of the selected cell structure are retrieved. The one or more stain colors of the selected cell structure are displayed. A selected stain color is received from the input device. The selected cell structure is displayed in the selected stain color in an exemplary cell image. Further, a three-dimensional image of a biological cell is stored. The three-dimensional image is displayed on a display that includes a touch screen. A movement selection is received from the touch screen. The three-dimensional image is displayed on the display according to the movement selection.

24 Claims, 19 Drawing Sheets

(56) References Cited

U.S. PATENT DOCUMENTS

| | | |
|---|---|---|
| 2009/0222746 A1* | 9/2009 | Chirica et al. ............... 715/762 |
| 2009/0273599 A1 | 11/2009 | Abasov et al. |
| 2009/0303233 A1 | 12/2009 | Lin et al. |
| 2011/0262907 A1* | 10/2011 | Peltier ............................ 435/6.1 |

OTHER PUBLICATIONS

Peng, Hanchuan et al., "V3D Enables Real-time 3D Visualization and Quantitative Analysis of Large-Scale Biological Data Sets", *Nature Biotechnology* 2010: 28 (4),p. 348-355.

* cited by examiner

FIG. 8

VIRTUAL CELLULAR STAINING

RELATED APPLICATIONS

This application claims the benefit under 35 U.S.C. §119(e) of U.S. Provisional Application Ser. No. 61/420,708 filed Dec. 7, 2010, U.S. Provisional Application Ser. No. 61/450,519 filed Mar. 8, 2011 and U.S. Provisional Application Ser. No. 61/541,375 filed Sep. 30, 2011. The disclosures of the above-identified applications are incorporated herein by reference as if set forth in full.

FIELD

The present disclosure generally relates to the imaging of biological materials and in particular to systems, methods, software and computer-usable media for virtual staining of cells and related structures.

INTRODUCTION

In an imaging experiment, dyes or stains are used to label different organelles or structures of a biological cell. These structures of a cell are stained to analyze or learn about a cell, for example. Often, two or more structures of a cell are stained at the same time. This is called multiplex staining. Crosstalk is the overlap or mixture of colors emitted from multiplex staining. If there is too much crosstalk in the colors emitted from multiplex staining, it may be impossible to distinguish individual structures. As a result, it may be impossible to identify or analyze a particular structure of a cell for an experiment.

Traditionally, in imaging experiments involving multiplex staining, crosstalk prevention has largely been achieved through a trial and error. Typically, reagents are purchased, a protocol is performed, a cell is stained and a compatible microscope is used to determine if crosstalk is apparent. These steps are then performed iteratively until a combination of stains is found that does not produce crosstalk. Such an approach often requires purchasing and using more reagents than is necessary and can also significantly increase the overall time needed to perform an imaging experiment.

SUMMARY

Systems and methods to create virtual cellular staining are provided. Specifically, techniques are provided for minimizing the color crosstalk between reagents used in multiplex staining applications.

In one aspect, a system for displaying one or more cell structures of a biological cell is provided. The system is comprised of a memory, an input device, a display and a processor. The memory is configured to store a plurality of cell structures of a biological cell and one or more stain colors for each cell structure. The processor is in communication with the memory, the input device and the display. The processor is further configured to: receive a selected cell structure from the input device, retrieve one or more stain colors of the selected cell structure from the memory, display the one or more stain colors of the selected cell structure on the display, receive a selected stain color from the input device and display the selected cell structure in the selected stain color in an exemplary cell image on the display that is representative of a staining of the selected cell structure in the selected stain color.

In one aspect, a method for displaying cell structures of a biological cell is provided. A plurality of cell structures of a biological cell and one or more stain colors for each cell structure are stored using a memory. A selected cell structure is received from an input device using a processor. One or more stain colors of the selected cell structure are retrieved from the memory using the processor. The one or more stain colors of the selected cell structure is displayed on a display using the processor. A selected stain color from the input device is received using the processor. The selected cell structure is displayed in the selected stain color in an exemplary cell image on the display that is representative of a staining of the selected cell structure in the selected stain color using the processor.

In one aspect, a computer program product, comprising a non-transitory and tangible computer-readable storage medium whose contents include a program with instructions being executed on a processor so as to perform a method for displaying cell structures of a biological cell is provided. A system is provided, wherein the system comprises one or more distinct software modules, and wherein the distinct software modules comprise a storage module and a stain module. A plurality of cell structures of a biological cell and one or more stain colors for each cell structure is stored in a memory using the storage module. A selected cell structure is received from an input device using the stain module. One or more stain colors of the selected cell structure is retrieved from the memory using the storage module. The one or more stain colors of the selected cell structure is displayed on a display using the stain module. A selected stain color is received from the input device using the stain module. The selected cell structure is displayed in the selected stain color in an exemplary cell image on the display that is representative of a staining of the selected cell structure in the selected stain color using the stain module.

In one aspect, a system for displaying one or more cell structures of a biological cell is provided. The system includes a memory and a processor. The memory is configured to store a plurality of cell structures of a biological cell and one or more stain colors for each cell structure. The processor is in communication with the memory and a client device. The processor is further configured to: receive a selected cell structure from the client device, retrieve one or more stain colors of the selected cell structure from the memory, communicate and display the one or more stain colors of the selected cell structure on the client device, receive a selected stain color from the input device and communicate and display the selected cell structure in the selected stain color in an exemplary cell image on the client device that is representative of a staining of the selected cell structure in the selected stain color.

In one aspect, a method for allowing a customer to order a reagent product is provided. A computer program product is provided comprising a processor for allowing customers to perform simulations involving the reagent product in a device. A selectable item corresponding to the reagent product is displayed on the computer program product and on the device, wherein when selected by the customer, the processor is configured to trigger an order of the reagent product. The triggered order of the reagent product is processed using the processor.

These and other features are provided herein.

BRIEF DESCRIPTION OF THE DRAWINGS

The skilled artisan will understand that the drawings, described below, are for illustration purposes only. The drawings are not intended to limit the scope of the present teachings in any way.

FIG. 8 is an exemplary screen shown after a reagent product is selected for the lysosomes cell structure and green stain color in a system for displaying structures of a biological cell, in accordance with various embodiments.

Figure 1:
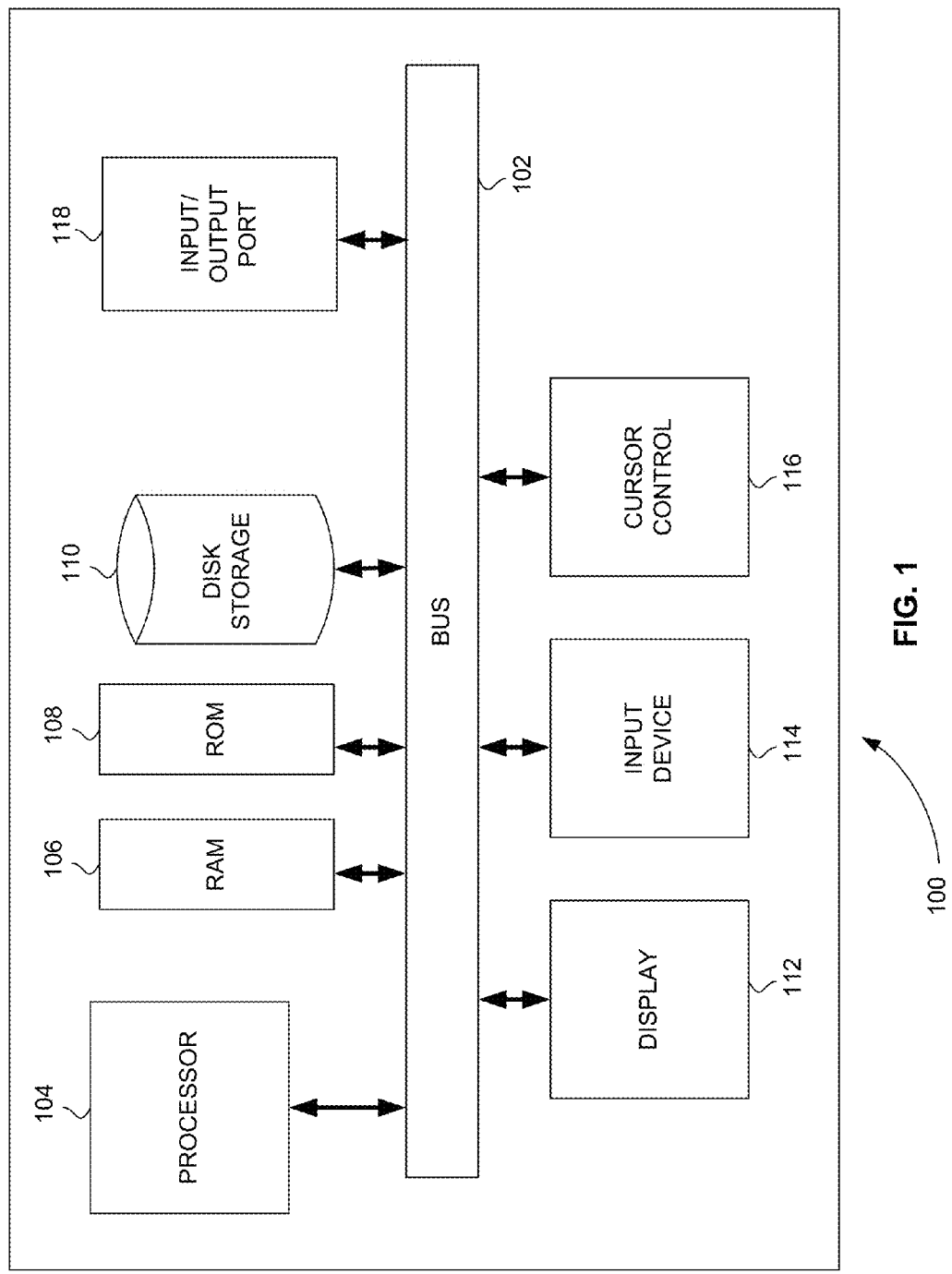
FIG. 1 is a block diagram that illustrates a system, upon which embodiments of the present teachings may be implemented.

Before one or more embodiments of the present teachings are described in detail, one skilled in the art will appreciate that the present teachings are not limited in their application to the details of construction, the arrangements of components, and the arrangement of steps set forth in the following detailed description or illustrated in the drawings. Also, it is to be understood that the phraseology and terminology used herein is for the purpose of description and should not be regarded as limiting.

DETAILED DESCRIPTION

System

FIG. 1 is a block diagram that illustrates a system 100, upon which embodiments of the present teachings may be implemented. System 100 can be, but is not limited to, a computer, a mobile phone, a tablet device, a gaming device, a music player, a video player, or a laboratory instrument. A computer can include any device capable of computing, and can include a workstation, a desktop computer, a laptop computer, for example. In various embodiments, system 100 can be a web or application server that can be configured to be in communications with one or more client devices through a network (e.g., LAN, WAN, Internet, etc.) connection (e.g., hardwire or wireless). For example, the system 100 can be communicatively connected, e.g., via Category 6 (CAT6), fiber optic, Wi-Fi, WLAN, etc., to a switch, router and/or web server (not shown) that is communicatively connected through the Internet to one or more client devices (not shown).

A tablet device can include any electronic device substantially shaped as a tablet, and can include the iPad®, a Windows-based tablet device, or an Android®-based tablet device, for example. A mobile phone device can include any device that can be carried by a user and that is capable of allowing the user to engage in a telephonic conversation, and can include the iPhone®, a Windows Phone™-based mobile phone, a WebOST™-based mobile phone, or an Android-based mobile phone, for example. A gaming device can include any device capable of allowing a user to play a video game and access the Internet, and can include the Playstation® device or the Wii® device, for example. A music player and a video player can include any device capable of playing music and video, respectively. A laboratory instrument can include any instrument suitable for use in a laboratory, and can include, for example, a genetic analyzer, a nucleic acid sequencer, a nucleic acid synthesizer, a nucleic acid purifier, a flow cytometer, a gene expression analyzer, a gene mapper, a cell analyzer, a cell counter, a digital microscope, etc.

In various embodiments, system 100 can include a bus 102 or other communication mechanism for communicating information, and a processor 104 coupled with bus 102 for processing information. System 100 can also include a memory 106, which can be a random access memory (RAM) or other dynamic storage device, coupled to bus 102 for determining base calls, and instructions to be executed by processor 104. Memory 106 also can be used for storing temporary variables or other intermediate information during execution of instructions to be executed by processor 104. System 100 can further include a read only memory (ROM) 108 or other static storage device coupled to bus 102 for storing static information and instructions for processor 104. A storage device 110, such as a magnetic disk or optical disk, can be provided and coupled to bus 102 for storing information and instructions.

System 100 can be coupled via bus 102 to a display 112, such as a cathode ray tube (CRT) or liquid crystal display (LCD), for displaying information to a user. An input device 114, which can include alphanumeric and other keys, can be coupled to bus 102 for communicating information and command selections to processor 104. Another type of user input device is a cursor control 116, such as a mouse, a trackball or cursor direction keys or a touch-sensitive pad or screen for communicating direction information and command selections to processor 104 and for controlling cursor movement on display 112. This input device typically has two degrees of freedom in two axes, a first axis (i.e., x) and a second axis (i.e., y), that allow the device to specify positions in a plane.

A system 100 can perform the present teachings. Consistent with certain implementations of the present teachings, results are provided by system 100 in response to processor 104 executing one or more sequences of one or more instructions contained in memory 106. Such instructions can be read into memory 106 from another computer-readable medium, such as storage device 110. Execution of the sequences of instructions contained in memory 106 can cause processor 104 to perform the process described herein. Alternatively hard-wired circuitry can be used in place of or in combination with software instructions to implement the present teachings. Thus, implementations of the present teachings are not limited to any specific combination of hardware circuitry and software.

The term "computer-readable medium" as used herein refers to any tangible and non-transitory medium that participates in providing instructions to processor 104 for execution. Such a medium may take many forms, including but not limited to, non-volatile media, volatile media, and transmission media. Non-volatile media include, for example, optical or magnetic disks, such as storage device 110. Volatile media includes dynamic memory, such as memory 106. Transmission media includes coaxial cables, copper wire, and fiber optics, including the wires that comprise bus 102.

Common forms of computer-readable media include, for example, a floppy disk, a flexible disk, a hard disk, a magnetic tape, or any other magnetic medium, a CD-ROM, any other optical medium, a punch card, a papertape, any other physical medium with patterns of holes, a RAM, a PROM, an EPROM, a FLASH-EPROM, any other memory chip or cartridge, or any other tangible and non-transitory medium from which a computer can read.

Various forms of computer readable media may be involved in carrying one or more sequences of one or more instructions to processor 104 for execution. For example, the instructions may initially be carried on the magnetic disk of a remote computer. The remote computer can load the instructions into its dynamic memory and send the instructions over a telephone line using a modem. A modem local to system 100 can receive the data on the telephone line and use an infra-red transmitter to convert the data to an infra-red signal. An infra-red detector coupled to bus 102 can receive the data carried in the infra-red signal and place the data on bus 102. Bus 102 can carry the data to memory 106, from which processor 104 retrieves and executes the instructions. The instructions received by memory 106 can be optionally be stored on storage device 110 either before or after execution by processor 104.

In accordance with various embodiments, instructions configured to be executed by a processor to perform a method are stored on a tangible and non-transitory computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

System 100 can also include input/output port 118. Input/output port 118 can be used to connect to a communications device. A communications device can include a wired or wireless network interface device. A wired or wireless network interface device can be connected to a network that is private or public. An exemplary public network is the Internet, for example. A wired or wireless network interface device can be connected to the Internet through one or more computers of one or more Internet service providers (ISPs). System 100 can be part of a system that can include, but is not limited to, a Web-based system, a cloud computing system, or a software as a service system (SAAS).

The following descriptions of various implementations of the present teachings have been presented for purposes of illustration and description. It is not exhaustive and does not limit the present teachings to the precise form disclosed. Modifications and variations are possible in light of the above teachings or may be acquired from practicing of the present teachings. Additionally, the described implementation includes software but the present teachings may be implemented as a combination of hardware and software or in hardware alone. The present teachings may be implemented with both object-oriented and non-object-oriented programming systems.

Systems and Methods of Data Processing

As described above, an imaging experiment that involves multiplex staining has traditionally required a trial and error approach to prevent crosstalk among emitted colors. In this approach, the steps of purchasing reagents, performing a protocol, staining a cell, and analyzing the emitted colors are executed iteratively to minimize or eliminate crosstalk. This approach can require purchasing and using more reagents than is necessary and can increase the overall time needed to perform an imaging experiment.

In various embodiments, systems and methods are used to create virtual cellular staining. This virtual cellular staining can be used to prevent or minimize crosstalk among emitted colors in an imaging experiment that involves multiplex staining, for example. Virtual cellular staining involves displaying one or more structures of an exemplary cell on a display of an electronic device and allowing a user to change the individual colors of the one or more structures of the cell. The colors of the one or more structures of the cell can be changed to colors emitted by known stains that are produced from known reagents for the one or more structures. This virtual cellular staining allows a user to apply a plurality of multiplex staining combinations without purchasing any reagents and without performing any laboratory protocols.

Figure 2:
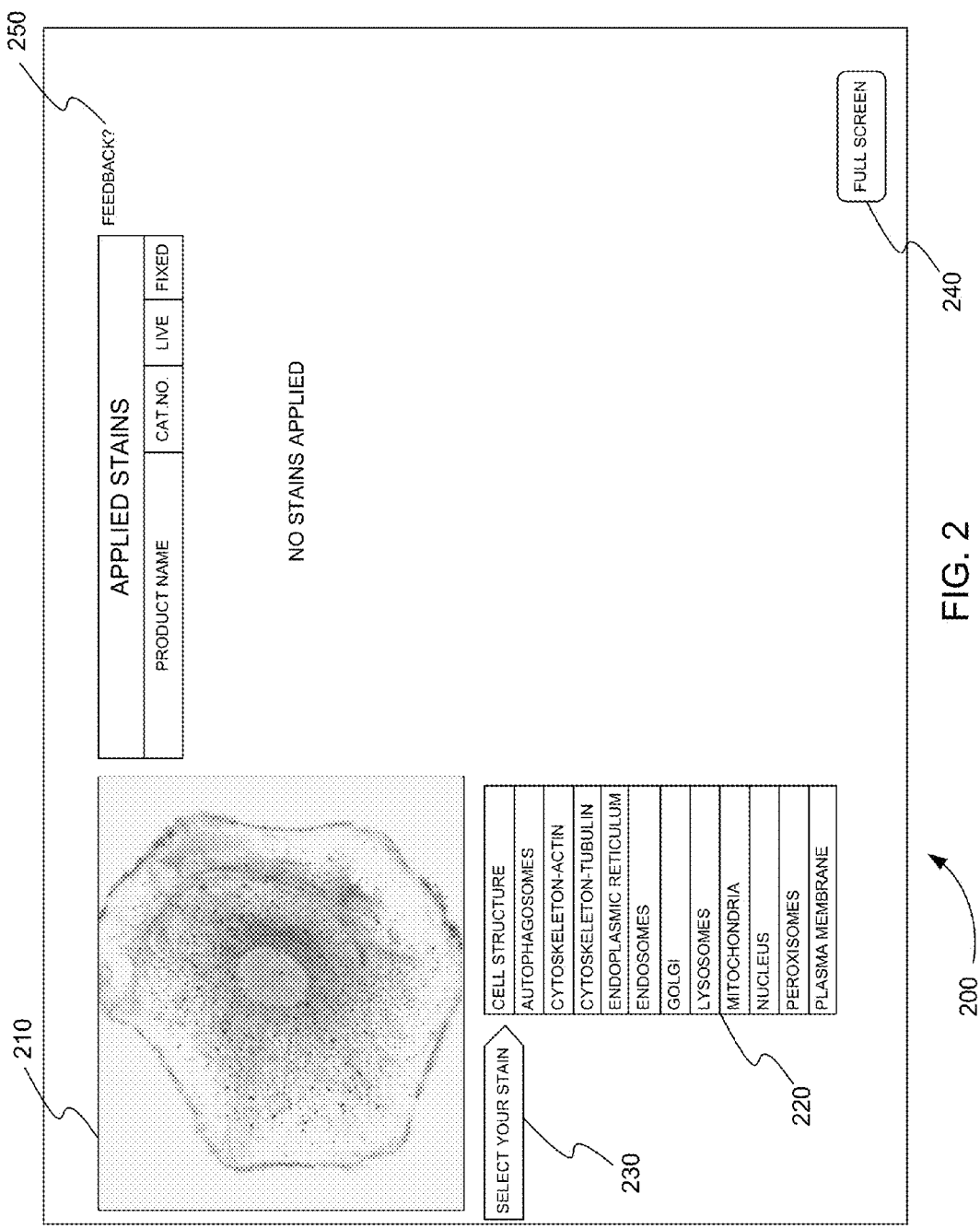
FIG. 2 is an exemplary initial screen of a system for displaying structures of a biological cell, in accordance with various embodiments.

FIG. 2 is an exemplary initial screen 200 of a system for displaying structures of a biological cell, in accordance with various embodiments. Screen 200 can include cell image area 210, cell structure menu 220, prompt 230, full screen button 240, and feedback link 250. In screen 200, an exemplary cell image is displayed in image area 210 that includes images of all of the cell structures available for staining. These cell structures are also listed as selectable menu items in cell structure menu 220. The cell structures displayed in cell image area 210 and listed in cell structure menu 220 can include, but are not limited to, autophagosomes, cytoskeleton-actin, cytoskeleton-tubulin, endoplasmic reticulum, endosomes, golgi, lysosomes, mitochondria, nucleus, peroxisomes, and plasma membrane.

The exemplary cell image displayed in image area 210 can be, for example, a compilation of two or more images of cell structures from one or more cells that are layered. The two or more images of cell structures can be generated from real cell images or images that are artificially created, for example. The exemplary cell image in image area 210 is designed to portray/display cell structures and what they would look like should a selected reagent be applied to stain the structures for viewing. The cell structures of the exemplary cell image in image area 210 can be shown in the same color and preferably a color not used for staining. The cell structures of the exemplary cell image can be shown, for example, in a white color on a black background. The cell structures of the exemplary cell image in image area 210 of FIG. 1 are shown in black on a white background for illustrative purposes.

Each of the cell structures listed in cell structure menu 220 is selectable. Prompt 230 encourages the selection of a cell structure listed in cell structure menu 220 in order to select a stain and begin virtual cellular staining. Full screen button 240 and feedback link 250 are also selectable. Full screen button 240 can make screen 200 or a portion of screen 200 occupy the entire screen of a display, for example. Feedback link 250 can provide communication to the developer of the virtual cellular staining. This communication can include, but is not limited to, email, chat, text, or hyperlinks. It can also include email, chat, text, or hyperlinks containing information regarding any feature or component of the system, including information about one or more characteristics of a product or reagent that may be ordered using the system.

Figure 3:
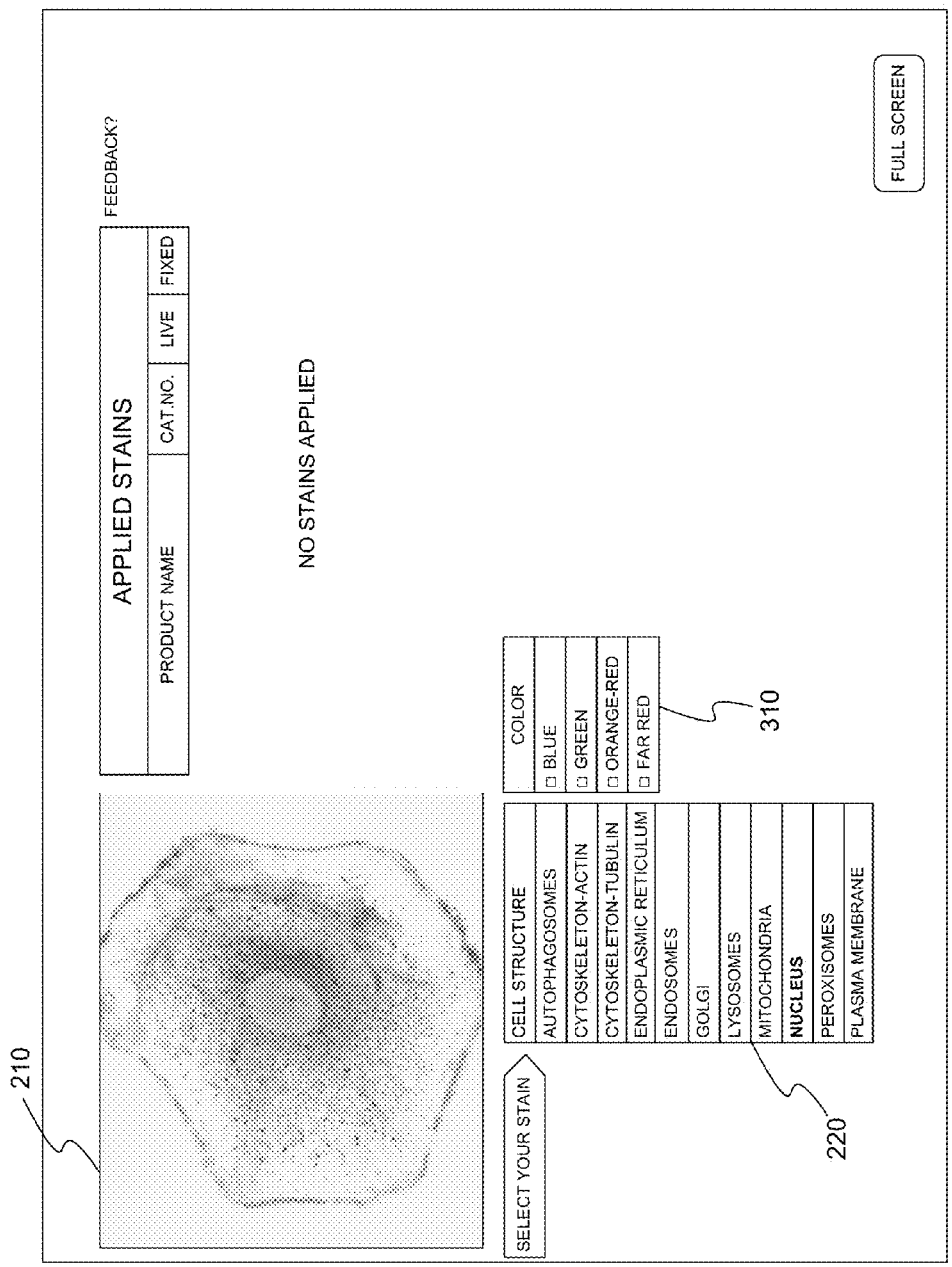
FIG. 3 is an exemplary screen shown after the nucleus cell structure is selected in a system for displaying structures of a biological cell, in accordance with various embodiments.

FIG. 3 is an exemplary screen 300 shown after the nucleus cell structure is selected in a system for displaying structures of a biological cell, in accordance with various embodiments. In screen 300, the stain colors available for staining the selected cell structure are shown in stain color menu 310. Stain colors are for example the emitted frequency or wavelength of light emitted from a cell structure after a cell staining protocol has been performed.

The stain colors available for staining the selected cell structure are determined from the reagents available from one or more reagent suppliers, for example. The stain colors available for staining the selected cell structure can also be determined from a spectrum of stain colors a cell structure is known to be able to emit. For example, as shown herein, the cell structure "NUCLEUS" is highlighted (bolded) in cell structure menu 220, showing that the cell structure "NUCLEUS" was selected. The stain colors available for the nucleus cell structure can include, but are not limited to, blue, green, orange-red, or far red.

Each of the stain colors listed in stain color menu 310 can be selected by a user. Selecting a stain color in stain color menu 310 continues the virtual cellular staining process. Because the cell structure "NUCLEUS" was selected from initial screen 200 shown in FIG. 2, image area 210 of FIG. 3 still depicts the exemplary cell image. In various embodiments, image area 210 of FIG. 3 can display an exemplary image of the selected cell structure in a color other than a stain color.

Figure 4:
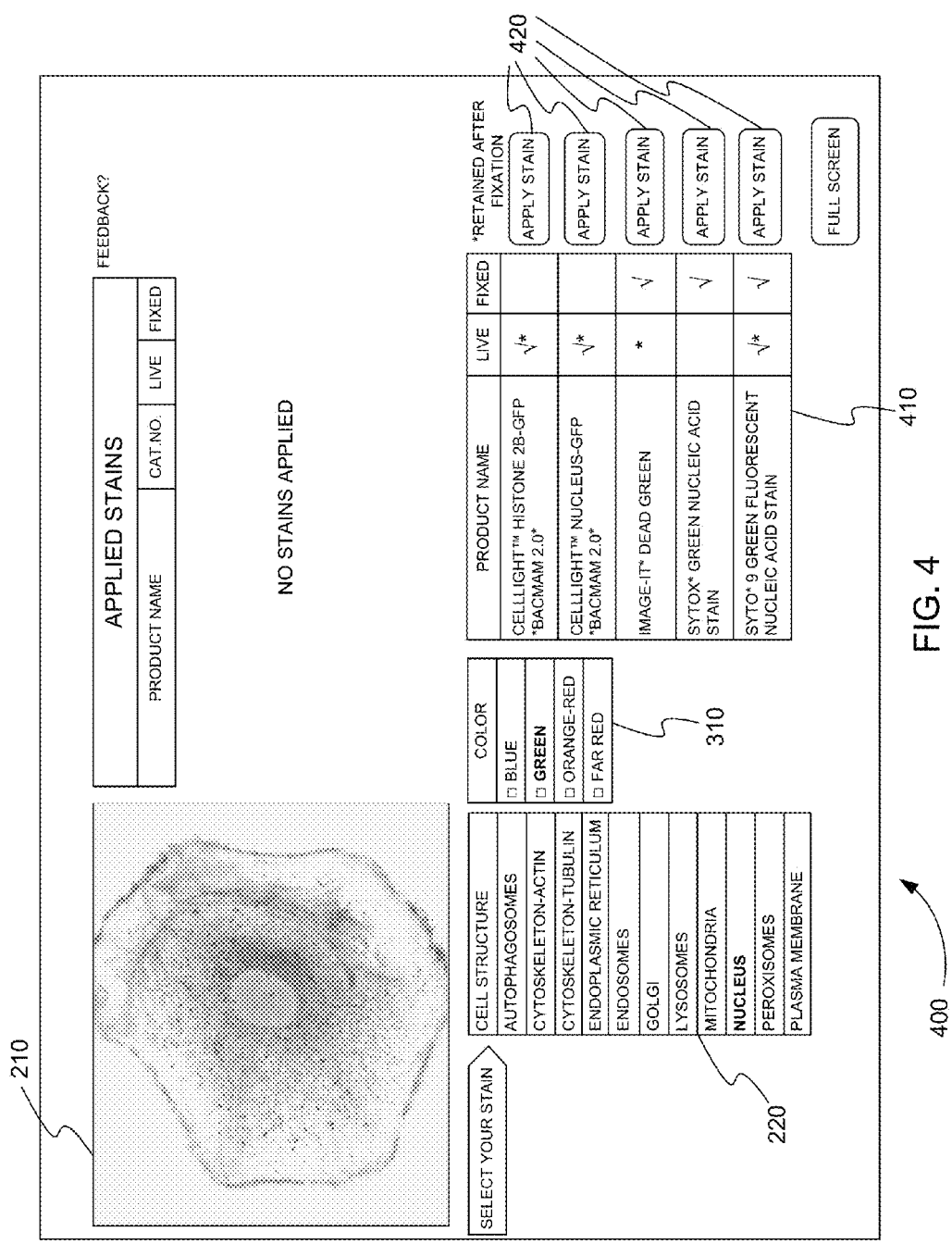
FIG. 4 is an exemplary screen shown after the nucleus cell structure and green stain color are selected in a system for displaying structures of a biological cell, in accordance with various embodiments.

FIG. 4 is an exemplary screen 400 shown after the nucleus cell structure and green stain color are selected in a system for displaying structures of a biological cell, in accordance with various embodiments. In screen 400, the reagent stain products available for staining the selected cell structure to achieve the desired stain color are shown in product menu 410. The products shown in product menu 410 are determined from the combination of the cell structure selected and the stain color selected.

In product menu 410 the name of each product is shown. Products can be used for one or more types of imaging experiments. As a result, each product shown in product menu 410 can also include one or more indicators that specify the one or more types of experiments that can be performed with that product. Types of experiments that can be performed with stain reagent products can include, but are not limited to, live cell applications, fixed cell applications, or applications where a live cell is retained after fixation.

Each of the product names listed in product menu 410 can be selectable. Selecting a product name in product menu 410 continues the virtual cellular staining process. A product can also be selected by pressing the adjacent apply stain button of apply stain buttons 420. As depicted herein, the cell structure "NUCLEUS" is highlighted in the cell structure menu 220 and the stain color "GREEN" is highlighted in the stain color menu 310 showing that the products in product menu 410 are available for the combination of a nucleus cell structure and a green stain color. An exemplary cell image is still shown in image area 210. In various embodiments and as described above, image area 210 can also display an exemplary image of the selected cell structure in a color other than the selected stain color.

Figure 5:
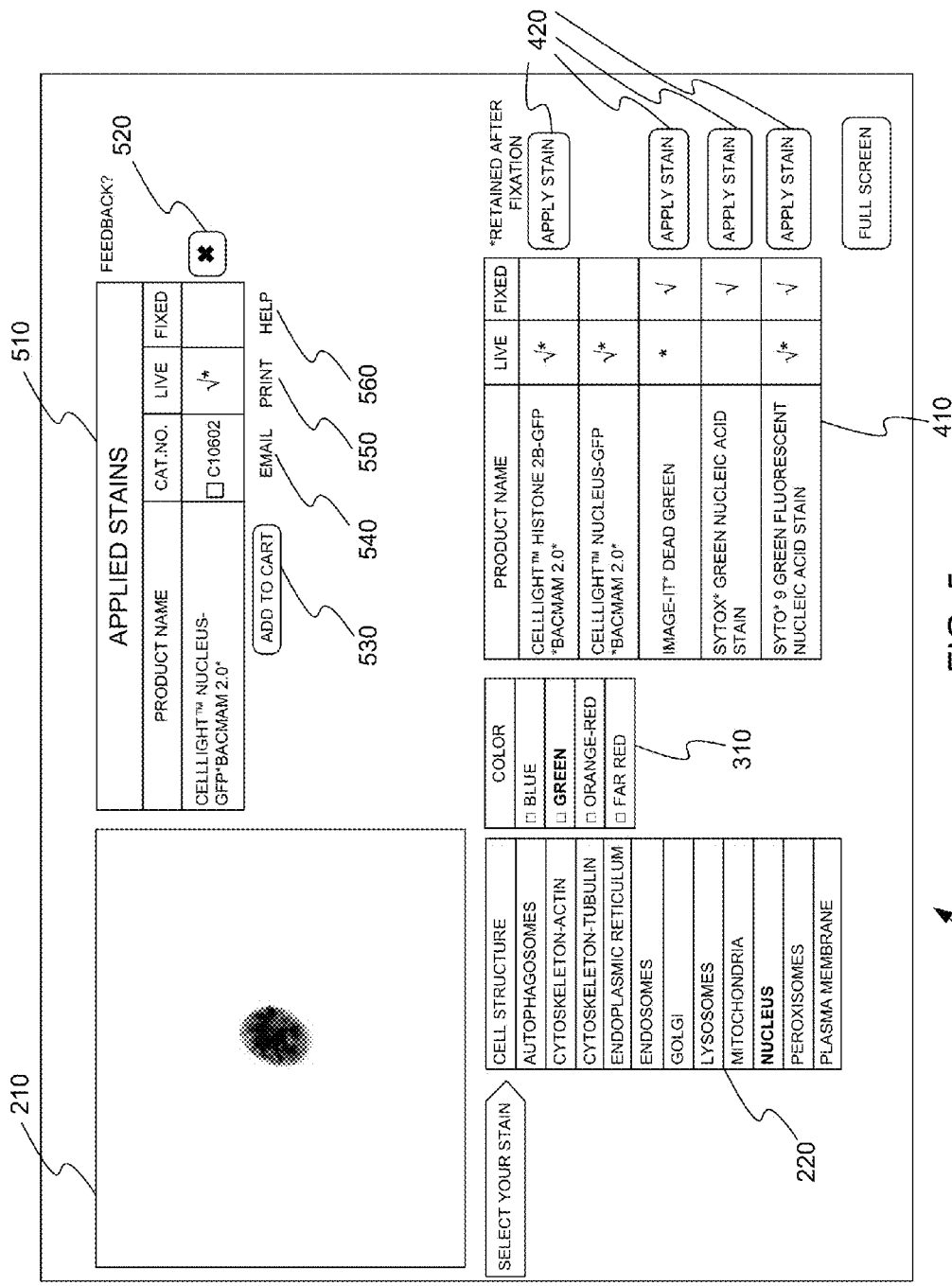
FIG. 5 is an exemplary screen shown after a reagent product is selected for the nucleus cell structure and green stain color in a system for displaying structures of a biological cell, in accordance with various embodiments.

FIG. 5 is an exemplary screen 500 shown after a reagent product is selected to stain the nucleus cell structure a green stain color in a system for displaying structures of a biological cell, in accordance with various embodiments. In screen 500, the selected reagent product is listed in applied stains menu 510. An image of the selected cell structure stained in the stain color of the selected reagent product is then displayed in image area 210. Finally, the apply stain button adjacent to the selected product in product menu 410 is removed to further show the reagent product that was selected. The product name in product menu 410 is also made to be no longer selectable.

In applied stains menu 510 the name of the selected product is shown and the type of experiment that can be performed by the selected product is indicated. In addition, a catalog number is made available from at least one supplier for the selected reagent product. The catalog number is selectable, for example. In various embodiments, selecting the catalog number provides communication to the supplier of the selected product so the more information about the particular product can be obtained. Selecting the product name in applied stains menu 510 can alternatively or additionally provide the same communication. This communication can include, but is not limited to, email, text, chat, or hyperlinks.

Adjacent to the selected product in applied stains menu 510 is de-selection button 520. De-selection button 520 can be used to remove the applied stain. Selecting the de-selection button removes the selected product from applied stains menu 510. The previous image can then be restored to image area 210 and the apply stain button can be returned adjacent to the de-selected product. In other words, selecting de-selection button 520 results in returning to screen 400 of FIG. 4, for example.

Screen 500 of FIG. 5 also provides a number of buttons or selectable items below applied stains menu 510. These buttons or selectable items can include, but are not limited to, add to cart button 530, email selection 540, print selection 550, and help selection 560. Add to cart button 530 allows a selected product to be added to an e-commerce shopping cart so that the selected product can be purchased. The shopping cart can be a shopping cart of the system for displaying structures of a biological cell or a shopping cart of a supplier of the selected product. Email selection 540 allows the selected product or any other information from screen 500 to be emailed, for example. Print selection 550 allows the selected product or any other information from screen 500 to be printed, for example. Help selection 560 provides help information on the selected product or any other information on screen 500, for example.

Only one selected product is shown listed in applied stains menu 510. Applied stains menu 510 can include two or more selected products. In various embodiments, the system for displaying structures of a biological cell can have a limit for the number of products that can be selected at one time. For example, the system may limit the number of selected products to four. Two or more selected products in applied stains menu 510 can be selected from any combination of cell structures in cell structure menu 220 and colors in stain color menu 310. For example, two or more selected products in applied stains menu 510 can be for the same cell structure and the same stain color, the same cell structure and different stain colors, different cell structures and the same stain color, or different cell structures and different stain colors.

For each selected product added or removed from applied stains menu 510, image area 210 can be updated with an image reflecting the combination of cell structures and stain colors that remain. The images of two or more cell structures can be layered on top of each other in image area 210. In various embodiments, the different colors of the products listed in applied stains menu 510 are mixed as different frequencies or wavelengths of light are mixed and displayed in image area 210 at the mixed frequency or wavelength. As a result, the addition of two products with two different stain colors can produce an image in image area 210 that has a third color, for example. In other words, the image displayed in image area 210 can show both multiplex and multimodal staining. The image is multiplexed in that it can show different combinations cell structures and it is multimodal in that it can show different combinations of stain colors.

Figure 6:
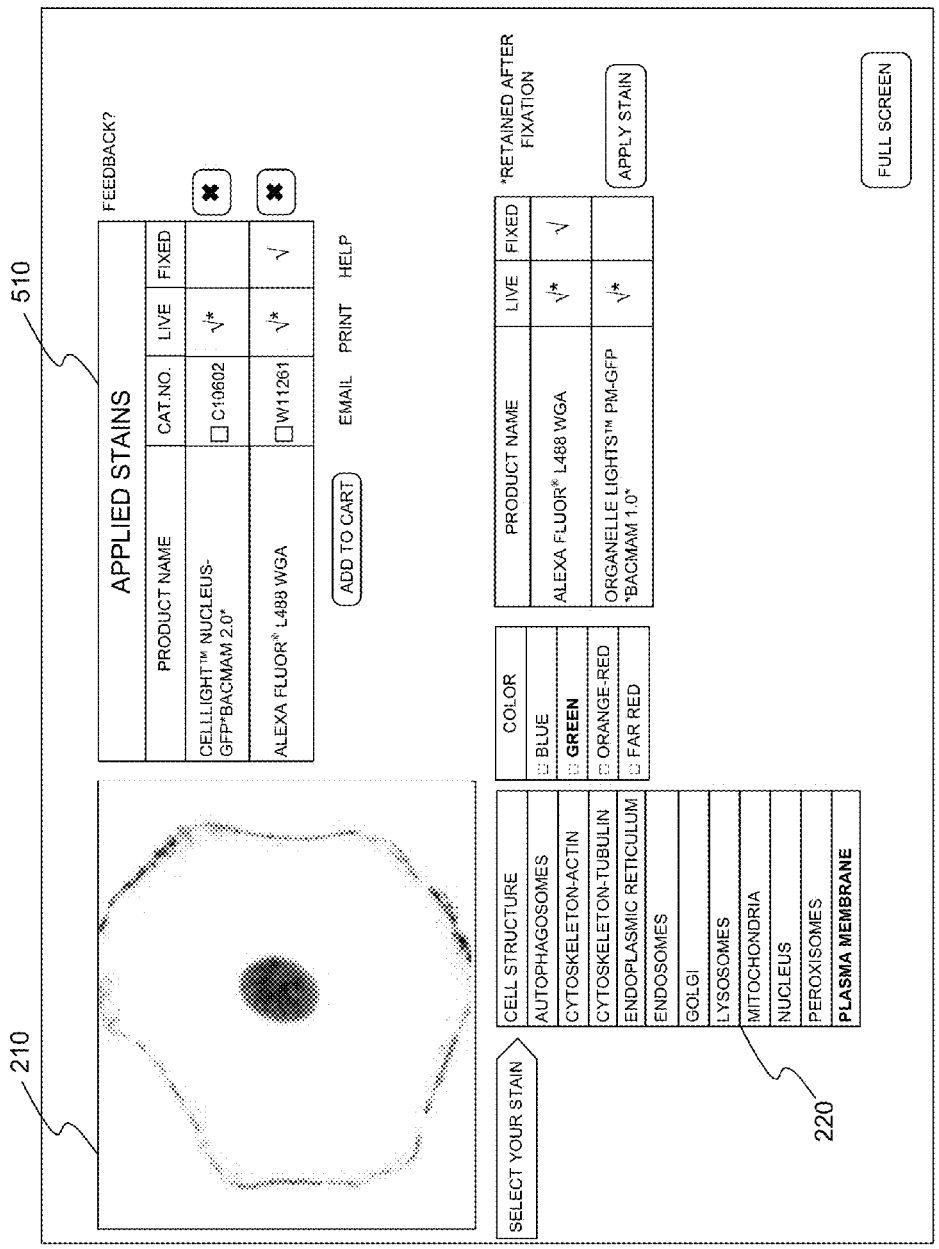
FIG. 6 is an exemplary screen shown after reagent products for the nucleus and plasma membrane cell structures are selected in a system for displaying structures of a biological cell, in accordance with various embodiments.

FIG. 6 is an exemplary screen 600 shown after reagent products for the nucleus and plasma membrane cell structures are selected in a system for displaying structures of a biological cell, in accordance with various embodiments. In screen 600, products for the nucleus and plasma membrane cell structures are shown listed in applied stains menu 510. Both of these products are for the stain color green. A layered stained image of the nucleus and plasma membrane cell structures can be displayed in image area 210. The stained image in image area 210 is an example of multiplex staining. In this example there is no apparent "crosstalk" or overlap in the colors emitted from the multiplex staining. The two cell structures are easily discernable, so it is not necessary to try different products for this combination of cell structures.

A plasma membrane cell structure can be combined with a nucleus cell structure by selecting "PLASMA MEMBRANE" in cell structure menu 220 of FIG. 5, for example. After selecting the green stain color and a plasma membrane reagent product, screen 600 of FIG. 6 is produced. A product for the nucleus is, therefore, selected before a product for the plasma membrane to produce screen 600 of FIG. 6. A similar screen to screen 600, however, can be produced by selecting a product for the plasma membrane before selecting a product for the nucleus. In other words, the image displayed in image area 210 is independent of the order in which products are selected.

Figure 7:
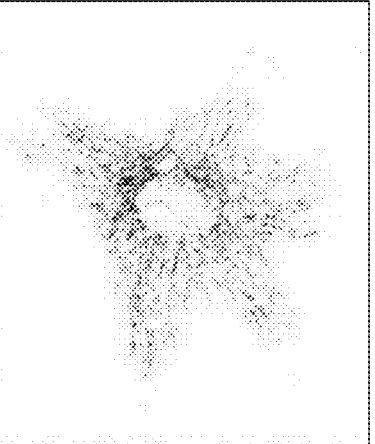
FIG. 7 is an exemplary screen shown after a reagent product is selected for the mitochondria cell structure and green stain color in a system for displaying structures of a biological cell, in accordance with various embodiments.

FIG. 7 is an exemplary screen 700 shown after a reagent product is selected for the mitochondria cell structure and green stain color in a system for displaying structures of a biological cell, in accordance with various embodiments. Applied stains menu 510 in screen 700 can include the product selected for the mitochondria cell structure and green stain color. An image of the mitochondria cell structure is shown in image area 210 in the green stain color of the selected product.

Figure 8:
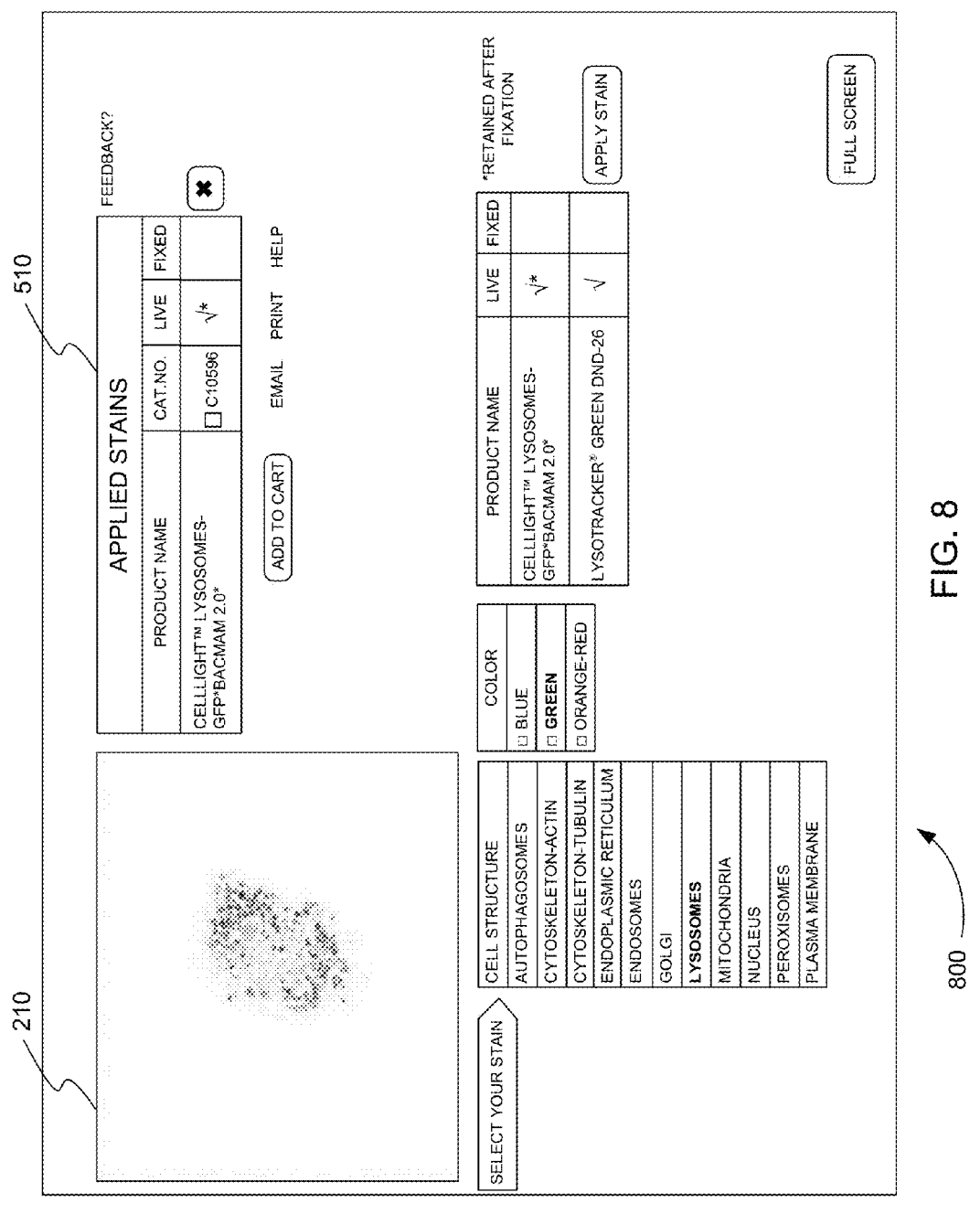

FIG. 8 is an exemplary screen 800 shown after a reagent product is selected for the lysosomes cell structure and green stain color in a system for displaying structures of a biological cell, in accordance with various embodiments. Applied stains menu 510 in screen 800 can include the product selected for the lysosomes cell structure and green stain color. An image of the lysosomes cell structure is shown in image area 210 in the green stain color of the selected product.

Figure 9:
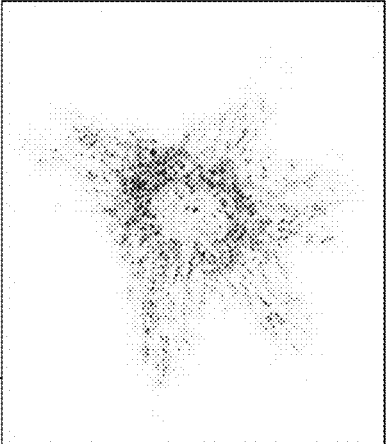
FIG. 9 is an exemplary screen shown after reagent products for the mitochondria and lysosomes cell structures are selected in a system for displaying structures of a biological cell, in accordance with various embodiments.

FIG. 9 is an exemplary screen 900 shown after reagent products for the mitochondria and lysosomes cell structures are selected in a system for displaying structures of a biological cell, in accordance with various embodiments. In screen 900, products for the mitochondria and lysosomes cell structures are shown listed in applied stains menu 510. Both of these reagent products are for the stain color green. A layered stained image of the mitochondria and lysosomes cell structures can also be displayed in image area 210. The stained image in image area 210 is also an example of multiplex staining. In this example, however, there is significant crosstalk between the colors emitted from the multiplex staining. Therefore, it is not possible to distinguish the mitochondria and lysosomes cell structures in image area 210.

Screen 900, however, can be used to find a stain color combination that eliminates this crosstalk. For example, either of the products listed in applied stains menu 510 can be de-selected. Using cell structure menu 220, color stain menu 310, and products menu 410, a product stain can be selected with an alternative color. This process can be repeated until a combination of colors is found that reduces or eliminates crosstalk between the colors emitted from the multiplex staining. This process can be completed without ordering reagents and running laboratory protocols. It can also be completed as quickly as the different product combinations can be selected. As a result, virtual cellular staining can reduce the cost and time of setting up imaging experiments.

Screen 900 can include image area 210 for viewing stained images of cell structures. Two or more screens like screen 900 can be displayed at the same time to compare one or more cell structures stained with different stain colors, for example. In various embodiments, screen 900 can include two or more image areas for comparing two or more stained images that are stained with different stain colors.

The virtual cellular staining outlined in FIGS. 2-9 can be used to analyze and learn about biological cells. A cell structure can be viewed in isolation or together with other cell structures. The spatial relationships between cell structures can be explored. Virtual cellular staining also shows the results of applying reagent products to cell structures and the many stain color combinations that can be produced. In addition, it reveals the capabilities and limitations of the products.

In various embodiments, a three-dimensional (3-D) image of a cell and its structures can be coupled with virtual cellular staining to further aid in analyzing and learning about cells. As described above, the images shown in FIGS. 2-9 are a compilation of two or more layers of 2-D images. Cell structures shown in close proximity in these 2-D images may actually be separated in three dimensions. A 3-D image can, therefore, provide insight into the proximity of cell structures by giving these layers a third dimension.

Figure 10:
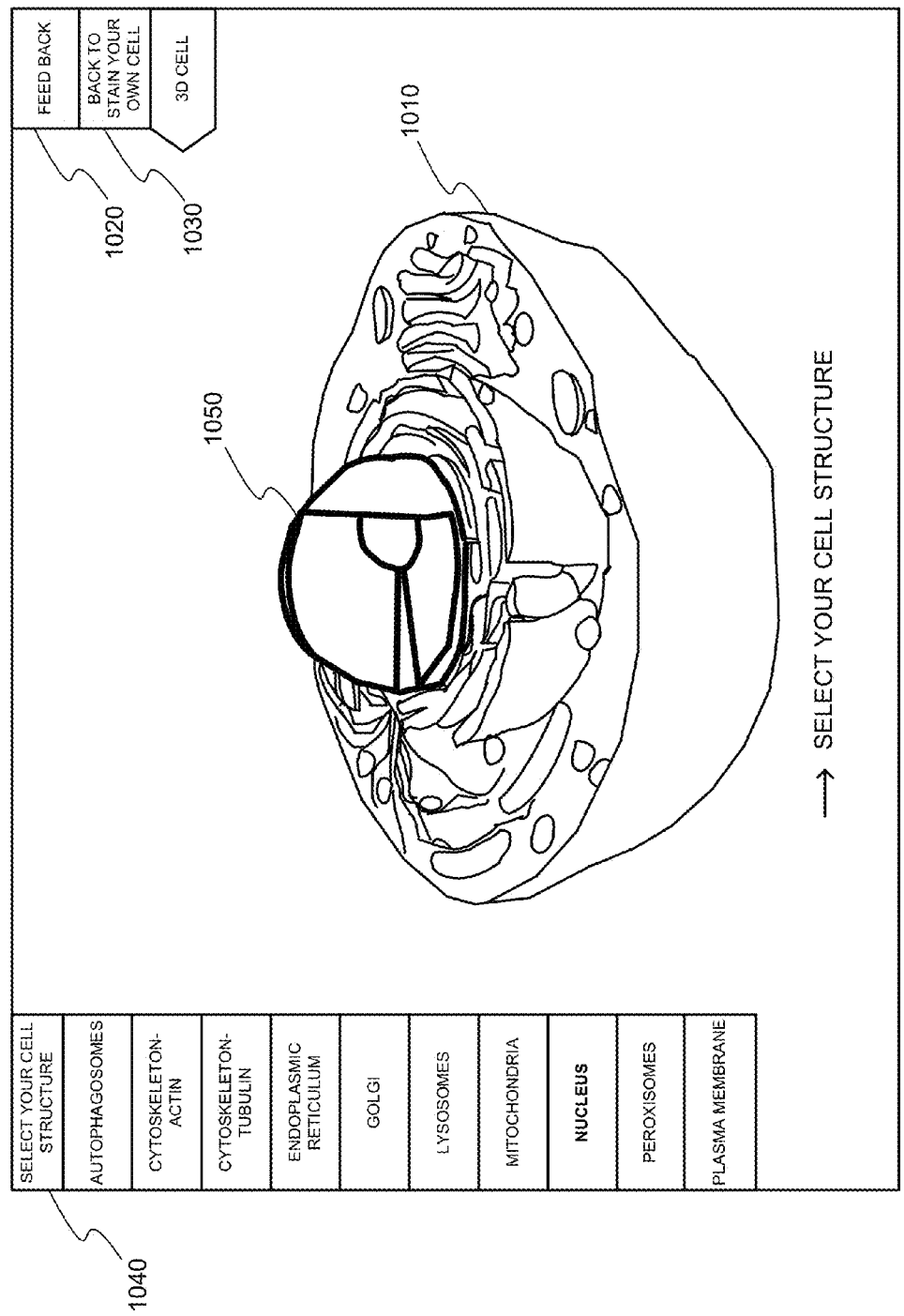
FIG. 10 is an exemplary initial screen of a system for displaying three-dimensional (3-D) cell structures of a biological cell, in accordance with various embodiments.

FIG. 10 is an exemplary initial screen 1000 of a system for displaying 3-D cell structures of a biological cell, in accordance with various embodiments. Screen 1000 can include a 3-D cell image 1010, feedback selection 1020, back to stain your own cell selection 1030, and cell structure menu 1040. 3-D cell image 1010 can provide a 3-D view of a cell and its internal cell structures. Color is used to further distinguish internal cell structures. 3-D cell image 1010 can be moveable. It can be panned, zoomed, tilted, or rotated, for example. 3-D cell image 1010 may be moved, for example, on the display of an electronic device by touching the image with one or more fingers, or with a cursor.

Figure 11:
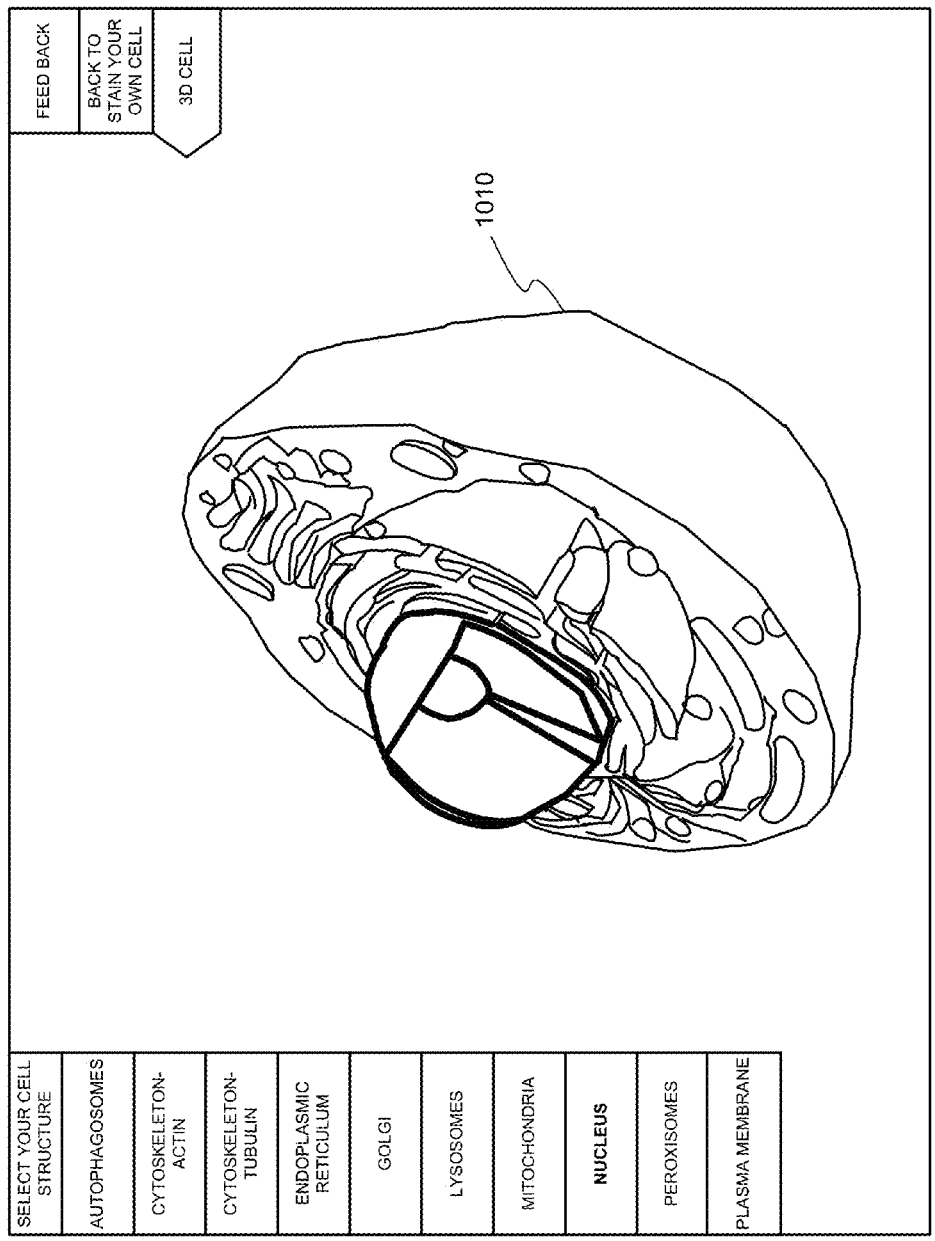
FIG. 11 is an exemplary screen of a system for displaying 3-D cell structures of a biological cell showing that a 3-D cell image can be tilted, in accordance with various embodiments.

FIG. 11 is an exemplary screen 1100 of a system for displaying 3-D cell structures of a biological cell showing that 3-D cell image 1010 can be tilted, in accordance with various embodiments.

Figure 12:
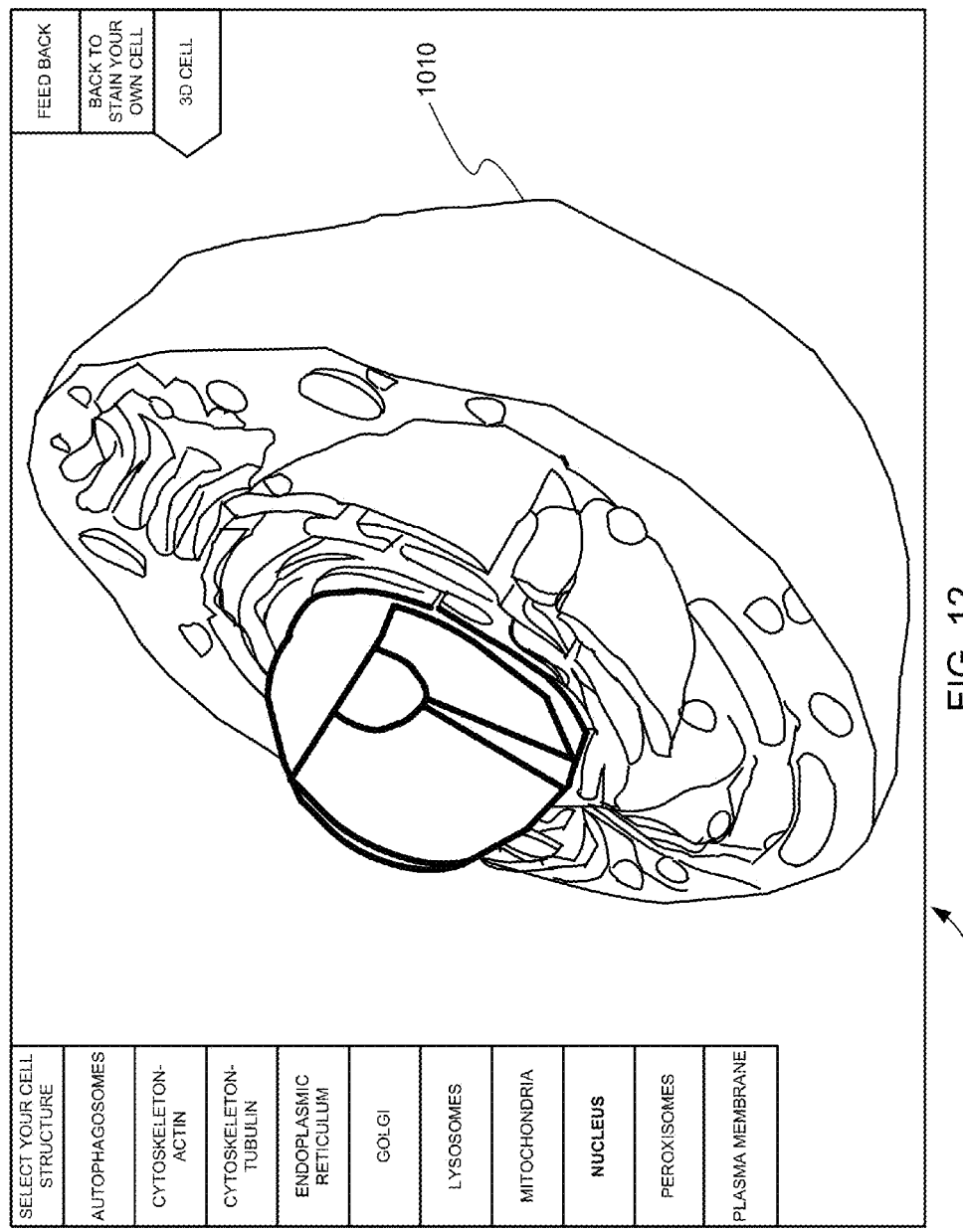
FIG. 12 is an exemplary screen of a system for displaying 3-D cell structures of a biological cell showing that a 3-D cell image can be tilted, panned, and zoomed, in accordance with various embodiments.

FIG. 12 is an exemplary screen 1200 of a system for displaying 3-D cell structures of a biological cell showing that 3-D cell image 1010 can be tilted, panned, and zoomed, in accordance with various embodiments.

Returning to FIG. 10, feedback selection 1020 provides communication to the developer of the system for displaying 3-D cell structures of a biological cell. This communication can include, but is not limited to, email, chat, text, or hyperlinks. Back to stain your own cell selection 1030 invokes virtual cell staining. Screen 200 in FIG. 2 is shown after selecting back to stain your own cell selection 1030, for example. The same cell structure selected in cell structure menu 1040 of FIG. 10 can be selected in Screen 200 of FIG. 2, for example.

Cell structures are listed as selectable menu items in cell structure menu 1040 of FIG. 10. The cell structures displayed in cell structure menu 1040 can include, but are not limited to, autophagosomes, cytoskeleton-actin, cytoskeleton-tubulin, endoplasmic reticulum, golgi, lysosomes, mitochondria, nucleus, peroxisomes, and plasma membrane. Selecting a cell structure in cell structure menu 1040 can cause that structure to be highlighted in 3-D cell image 1010. For example, the cell structure "NUCLEUS" can be selected and highlighted in cell structure menu 1040. This, in turn, can cause the nucleus cell structure 1050 to be highlighted in 3-D cell image 1010.

Therefore, cell structures can be highlighted in 3-D cell image 1010 using cell structure menu 1040. As described above, 3-D cell image 1010 can be moved by selecting the image. In various embodiments and alternatively, cell structures can be highlighted in 3-D cell image 1010 by selecting the structures in the image, and 3-D cell image 1010 can be moved by selecting movement functions from a menu.

In various embodiments and alternatively, cell structure menu 1040 can be used to provide more information on a selected cell structure. This information can include an exemplary stained 2-D image of the cell structure, a description of the cell structure and a listing of reagent products that can be used to stain a cell to view the cell structure. Viewing a stained 2-D image of selected cell structure immediately after viewing the same cell structure in 3-D helps in understanding the stained 2-D image.

Figure 13:
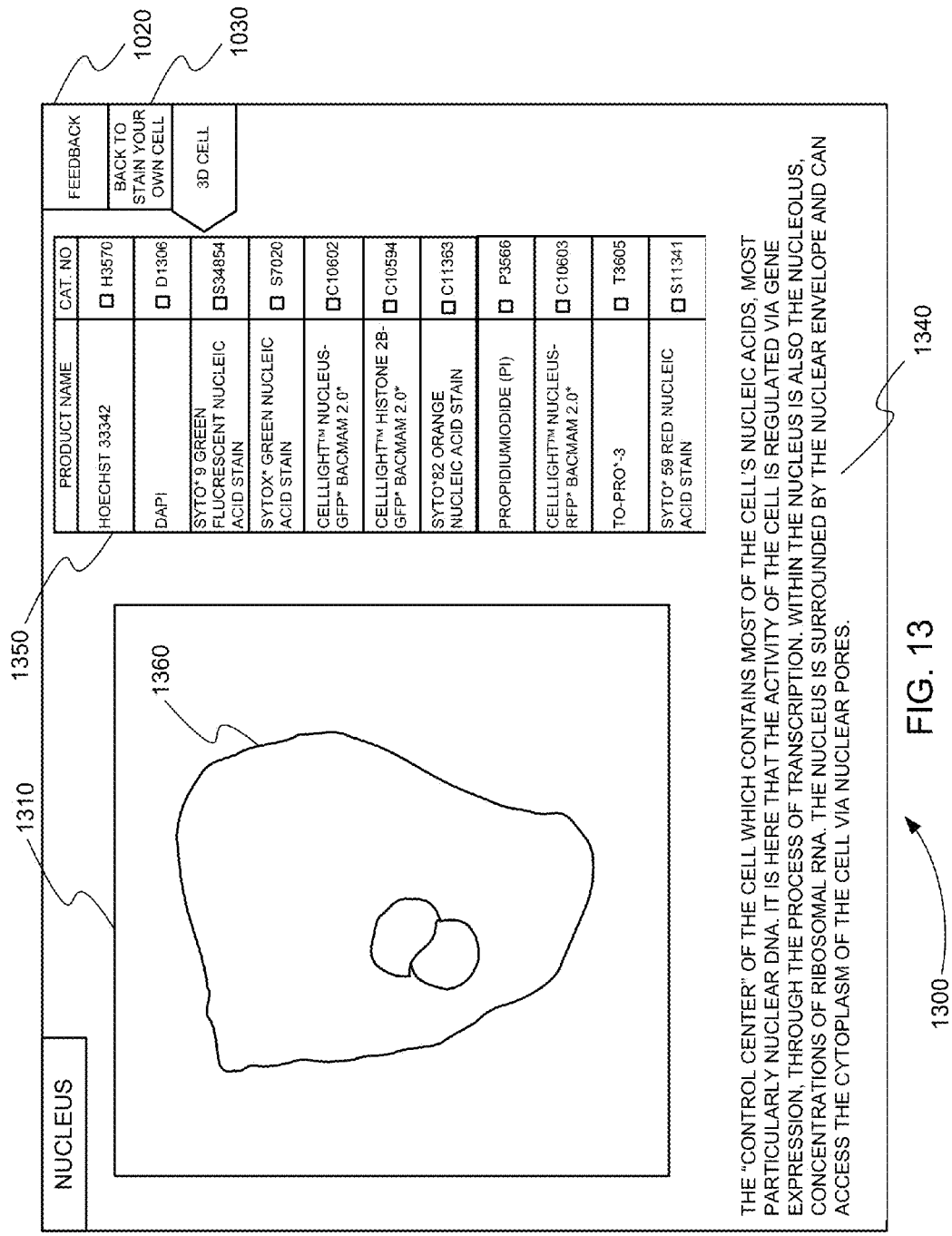
FIG. 13 is an exemplary screen of a system for displaying 3-D cell structures of a biological cell showing information on a cell structure, in accordance with various embodiments.

FIG. 13 is an exemplary screen 1300 of a system for displaying 3-D cell structures of a biological cell showing information on a cell structure, in accordance with various embodiments. Screen 1300 can include 2-D cell structure image 1310, feedback selection 1020, back to stain your own cell selection 1030, cell structure description 1340, and reagent product menu 1350. 2-D cell structure image 1310 is an exemplary 2-D stained image of the selected cell structure. 2-D cell structure image 1310 is shown as line drawing of nucleus 1360. In various embodiments, the features of nucleus 1360 are shown with an exemplary color stain on a black background.

As described above, feedback selection 1020 can provide communication to the developer of the system for displaying 3-D cell structures of a biological cell. Back to stain your own cell selection 1030 invokes virtual cell staining. Cell structure description 1340 can be a textual description of the selected cell structure.

Reagent product menu 1350 can be a list of the reagent products available from one or more suppliers to stain the selected cell structure. Reagent product menu 1350 includes a product name and catalog number. Selecting either the product name or catalog number can provide more information about the product. This information can come from the system for displaying 3-D cell structures of a biological cell or a product supplier, for example.

Virtual cellular staining as shown in FIGS. 2-9 and systems and methods for displaying 3-D cell structures are useful tools for analyzing and learning about cells and cell structures. These tools are useful for a large number of customers including, but not limited to, researchers, reagent products suppliers, health care providers, students, and educators. Further, placing these tools on mobile electronic devices increases their usefulness. Mobile devices that can display these tools can include, but are not limited to, tablet devices, cellular phones, music players, game devices, or mobile computers. Selections can be made and images can be manipulated using touch screens, pointing devices, or keyboards of these mobile devices, for example.

Virtual Cellular Staining System

FIG. 1 is a block diagram that illustrates a system 100, upon which embodiments of the present teachings may be implemented. A system for displaying cell structures of a biological cell can include a memory, an input device, a display, and a processor. The system can be, for example, a computer, a tablet device, or a mobile phone. The system can connected to a network or can operate without a connection. The memory can include, but is not limited to, RAM 106, ROM 108, or disk storage 110 of system 100. The input device can include, but is not limited to, input device 114 or another device connected to input/output port 118. The input device is, for example, a pointing device or a touch screen of the display. The display can include, but is not limited to, display 112. The display is, for example, an electronic display. The processor can be, but is not limited to, processor 104. The processor is, for example, a microprocessor, signal processor, application specific integrated circuit, or field programmable gate array.

The memory can store a plurality of cell structures of a biological cell. It can also store one or more stain colors for each cell structure of the plurality of cell structures.

The processor can be in communication with the memory, the input device, and the display. The processor can receive a selected cell structure from the input device. The input device can be, for example, a touch screen of the display. The processor can retrieve one or more stain colors of the selected cell structure from the memory. The processor can display the one or more stain colors of the selected cell structure on the display. The processor can receive a selected stain color from the input device. Finally, the processor can display the selected cell structure in the selected stain color in an exemplary cell image on the display that is representative of a staining of the selected cell structure in the selected stain color in an imaging experiment. The exemplary cell image is, for example, a compilation of two or more cell images.

In various embodiments, the system can also display information about staining reagent products. The memory can further store, for each stain color of the one or more stain colors, one or more reagent products that can produce the stain color. The processor can further retrieve one or more reagent products of the selected stain color from the memory. The processor can display the one or more reagent products of the selected stain color on the display. The processor can receive a selected reagent product from the input device. Finally, the processor can display the selected reagent product on the display. In various embodiments, the processor can further display the selected reagent product on the display as a selectable item that when selected provides more information on the selected reagent product. In various embodiments, the processor can further display a selectable item on the display that when selected begins a process of ordering the selected reagent product.

In various embodiments, the system can show if there is crosstalk between emissions from stains of different cell structures. The processor can further receive a second selected cell structure from the input device. The second selected cell structure is not the same cell structure as the selected cell structure selected earlier. The processor can retrieve one or more stain colors of the second selected cell structure from the memory. The processor can display the one or more stain colors of the second selected cell structure on the display. The processor can receive a second selected stain color from the input device. The processor can display the second selected cell structure in the second selected stain color in the exemplary cell image on the display in order to show if there is crosstalk between the previously selected stain color and the second selected stain color.

Virtual Cellular Staining Method

Figure 14:
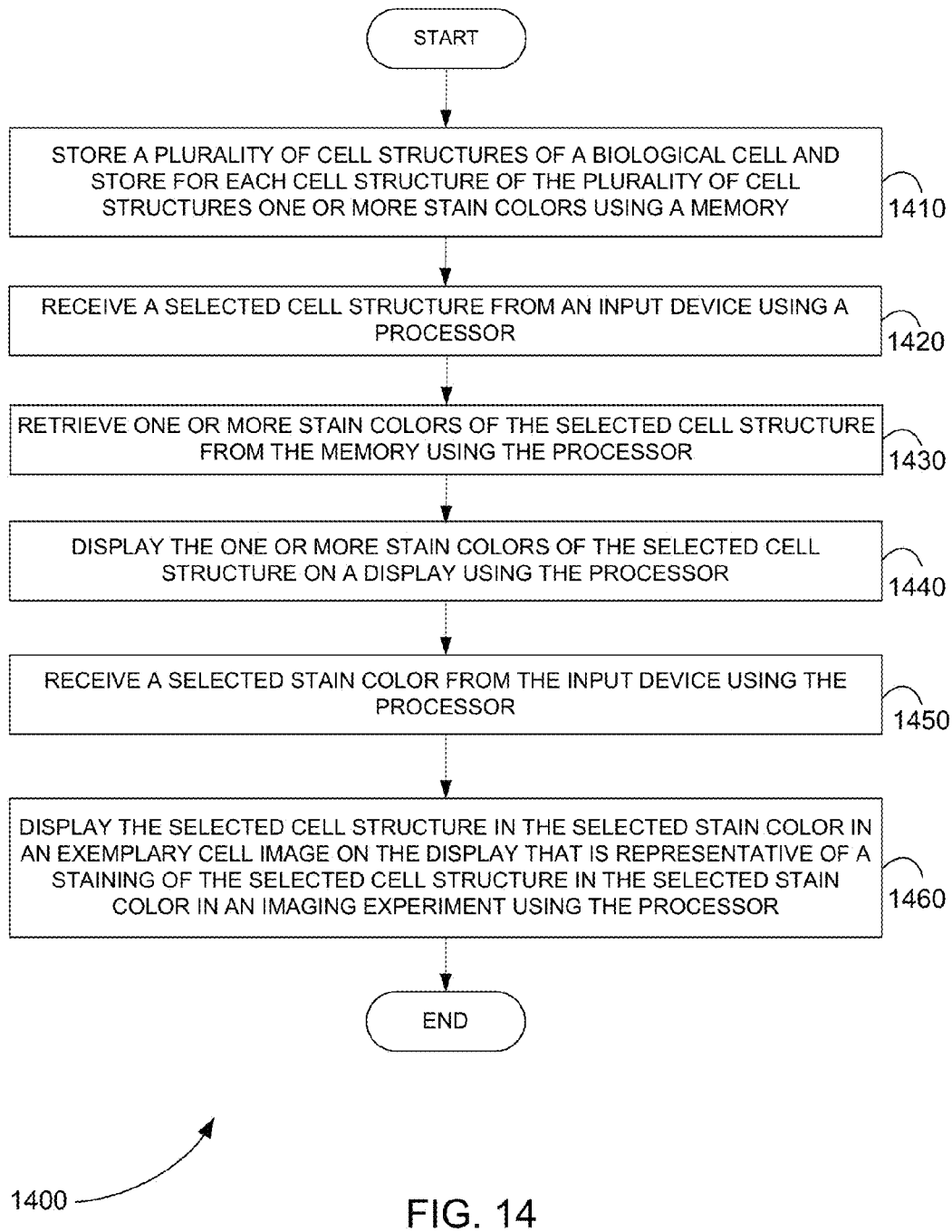
FIG. 14 is an exemplary flowchart showing a method for displaying cell structures of a biological cell, in accordance with various embodiments.

FIG. 14 is an exemplary flowchart showing a method 1400 for displaying cell structures of a biological cell, in accordance with various embodiments.

In step 1410 of method 1400, a plurality of cell structures of a biological cell are stored and for each cell structure of the plurality of cell structures one or more stain colors are stored using a memory.

In step 1420, a selected cell structure is received from an input device using a processor.

In step 1430, one or more stain colors of the selected cell structure are retrieved from the memory using the processor.

In step 1440, the one or more stain colors of the selected cell structure are displayed on a display using the processor.

In step 1450, a selected stain color is received from the input device using the processor.

In step 1460, the selected cell structure is displayed in the selected stain color in an exemplary cell image on the display using the processor. The image displayed is representative of a staining of the selected cell structure in the selected stain color.

Virtual Cellular Staining Computer Program Product

In various embodiments, a computer program product includes a non-transitory and tangible computer-readable storage medium whose contents include a program with instructions being executed on a processor so as to perform a method for displaying cell structures of a biological cell. This method is performed by a system that includes one or more distinct software modules.

Figure 15:
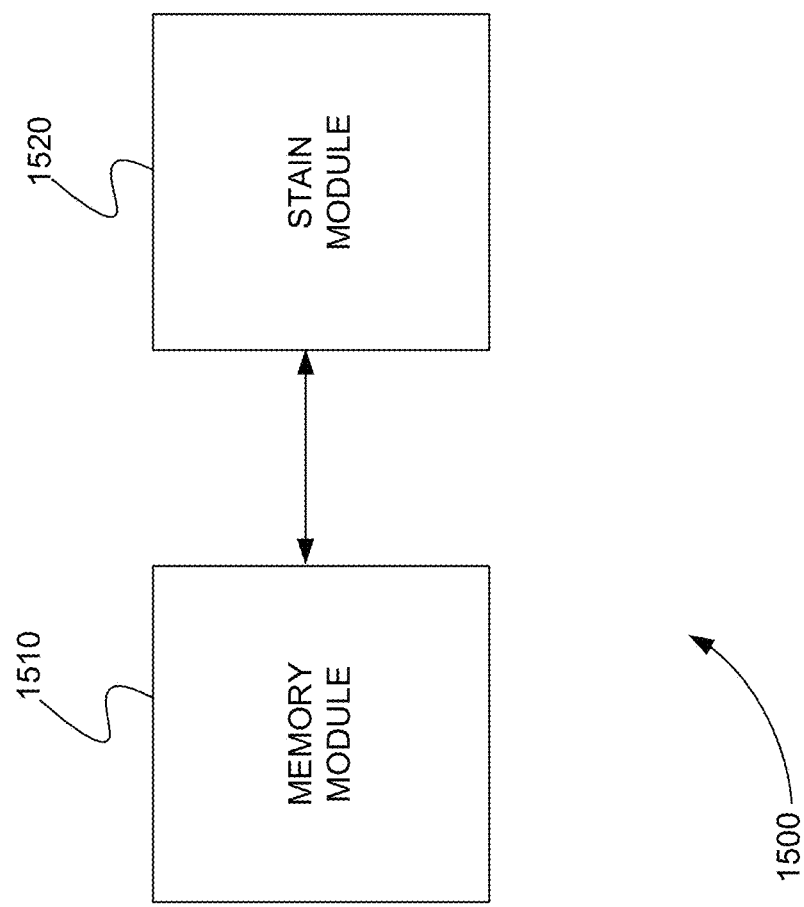
FIG. 15 is a schematic diagram of a system that includes one or more distinct software modules that performs a method for displaying cell structures of a biological cell, in accordance with various embodiments.

FIG. 15 is a schematic diagram of a system 1500 that includes one or more distinct software modules that performs a method for displaying cell structures of a biological cell, in accordance with various embodiments. In various embodiments, system 1500 can include a storage module 1510 and a stain module 1520.

Storage module 1510 can store a plurality of cell structures of a biological cell and store for each cell structure of the plurality of cell structures one or more stain colors in a memory. Stain module 1520 can receive a selected cell structure from an input device. Storage module 1510 can retrieve one or more stain colors of the selected cell structure from the memory. Stain module 1520 can display the one or more stain colors of the selected cell structure on a display. Stain module can 1520 receive a selected stain color from the input device. Stain module 1520 can display the selected cell structure in the selected stain color in an exemplary cell image on the display. The displayed image is representative of a staining of the selected cell structure in the selected stain color in an imaging experiment.

It should also be appreciated that the various modules/engines shown as being part of the system 1500 can be combined or collapsed into a single module/engine/data store, depending on the requirements of the particular application or system architecture. Moreover, in various embodiments, the system 1500 can comprise additional modules, engines, components or data stores as needed by the particular application or system architecture.

3-D Cell Display System

FIG. 1 is a block diagram that illustrates a system 100, upon which embodiments of the present teachings may be implemented. A system for displaying three-dimensional cell structures of a biological cell can include a memory, a display that includes a touch screen, and a processor. The system can be, for example, a computer, a tablet device, or a mobile phone. The system can be connected to a network or can operate without a connection. The memory can include, but is not limited to, RAM 106, ROM 108, or disk storage 110 of system 100. The touch screen can include, but is not limited to, input device 114 or another device connected to input/output port 118. The display can include, but is not limited to, display 112. The display can be, for example, an electronic display. The processor can be, but is not limited to, processor 104. The processor is, for example, a microprocessor, signal processor, application specific integrated circuit, or field programmable gate array.

The memory can store a three-dimensional image of a biological cell that includes three-dimensional cell structures. The processor can display the three-dimensional image on the display. The processor can receive a movement selection from the touch screen. The movement selection can include, but is not limited to, one of pan, tilt, rotate, or zoom. Finally, the processor can display the three-dimensional image on the display according to the movement selection to show a different view of the three-dimensional cell structures.

In various embodiments, a cell structure can be selected and highlighted in the three-dimensional image. The memory further can store a plurality of cell structures. The processor can further retrieve the plurality of cell structures from the memory. The processor can display the plurality of cell structures on the display. The processor can receive a selected cell structure from the touch screen. Finally, the processor can display the three-dimensional image with the selected cell structure highlighted on the display.

In various embodiments, a cell structure can be selected and more information is provided about the cell structure. The memory can further store a plurality of cell structures. The processor can further retrieve the plurality of cell structures from the memory. The processor can display the plurality of cell structures on the display. The processor can receive a selected cell structure from the touch screen. Finally, the processor can display a screen with information about the selected cell structure on the display. The information can include a two-dimensional stained image of the selected cell structure, for example. The information can include one or more reagent products that can be used to stain the selected cell structure, for example.

3-D Cell Display Method

Figure 16:
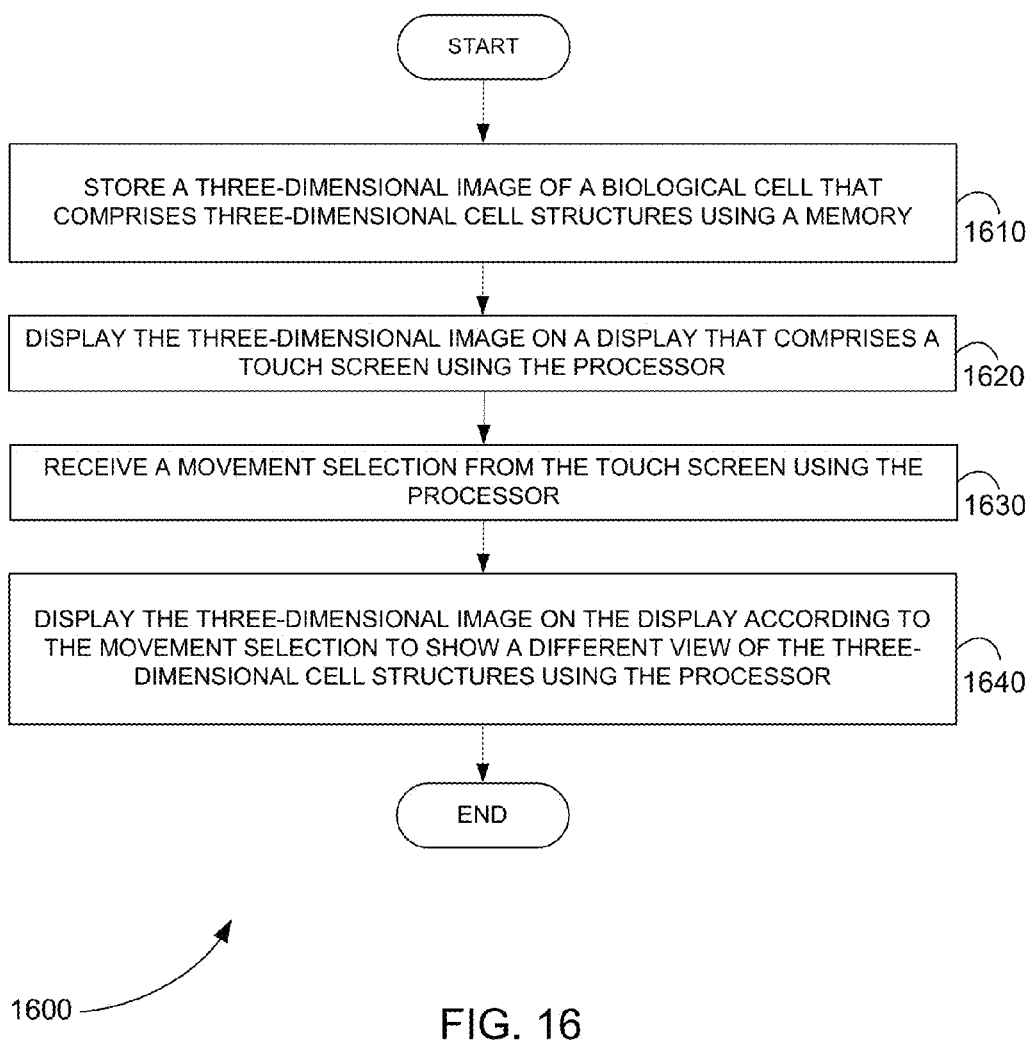
FIG. 16 is an exemplary flowchart showing a method for displaying three-dimensional cell structures of a biological cell, in accordance with various embodiments.

FIG. 16 is an exemplary flowchart showing a method 1600 for displaying three-dimensional cell structures of a biological cell, in accordance with various embodiments.

In step 1610 of method 1600, a three-dimensional image of a biological cell that includes three-dimensional cell structures can be stored using a memory.

In step 1620, the three-dimensional image can be displayed on a display that includes a touch screen using the processor.

In step 1630, a movement selection can be received from the touch screen using the processor.

In step 1640, the three-dimensional image can be displayed on the display according to the movement selection to show a different view of the three-dimensional cell structures using the processor.

3-D Cell Display Computer Program Product

In various embodiments, a computer program product includes a non-transitory and tangible computer-readable storage medium whose contents include a program with instructions being executed on a processor so as to perform a method for displaying three-dimensional cell structures of a biological cell. This method is performed by a system that can include one or more distinct software modules.

Figure 17:
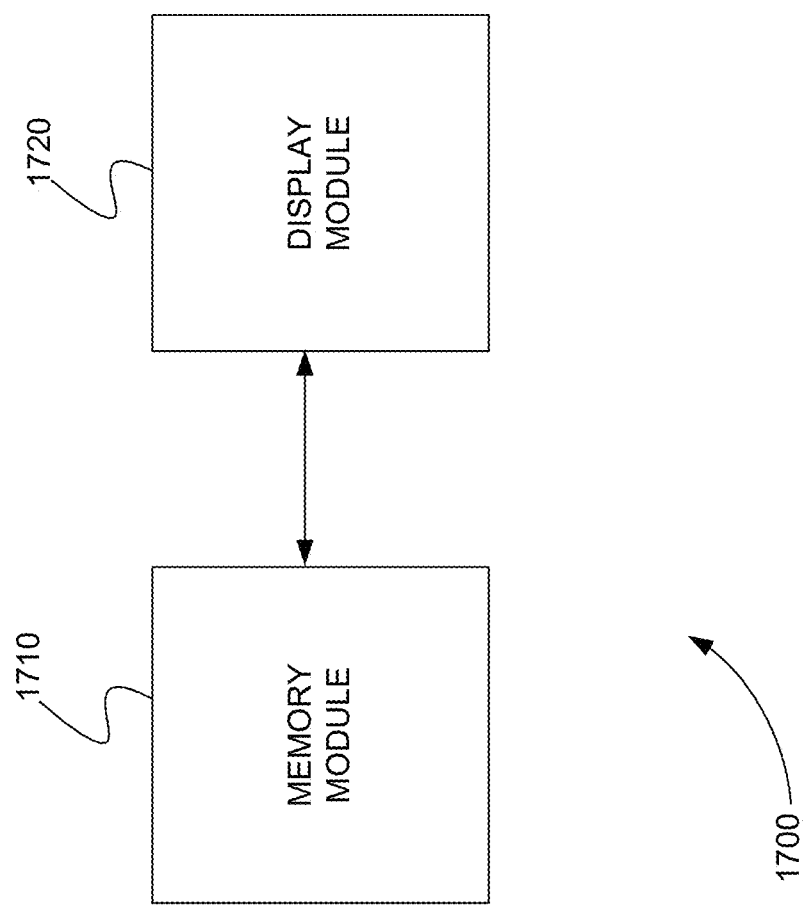
FIG. 17 is a schematic diagram of a system that includes one or more distinct software modules that performs a method for displaying three-dimensional cell structures of a biological cell, in accordance with various embodiments.

FIG. 17 is a schematic diagram of a system 1700 that can include one or more distinct software modules that performs a method for displaying three-dimensional cell structures of a biological cell, in accordance with various embodiments. System 1700 can include a storage module 1710 and a display module 1720.

Storage module 1710 can store a three-dimensional image of a biological cell that includes three-dimensional cell structures. Display module 1720 can display the three-dimensional image on a display that includes a touch screen. Display module 1720 can receive a movement selection from the touch screen using the display module. Display module 1720 can display the three-dimensional image on the display according to the movement selection. The three-dimensional image then shows a different view of the three-dimensional cell structures.

Reagent Product Methods

In various embodiments, a benchtop instrument, such as a digital microscope for example, can be running an application from which a user can run a simulation and obtain marketing info about and/or order reagents involved in that simulation.

Figure 18:
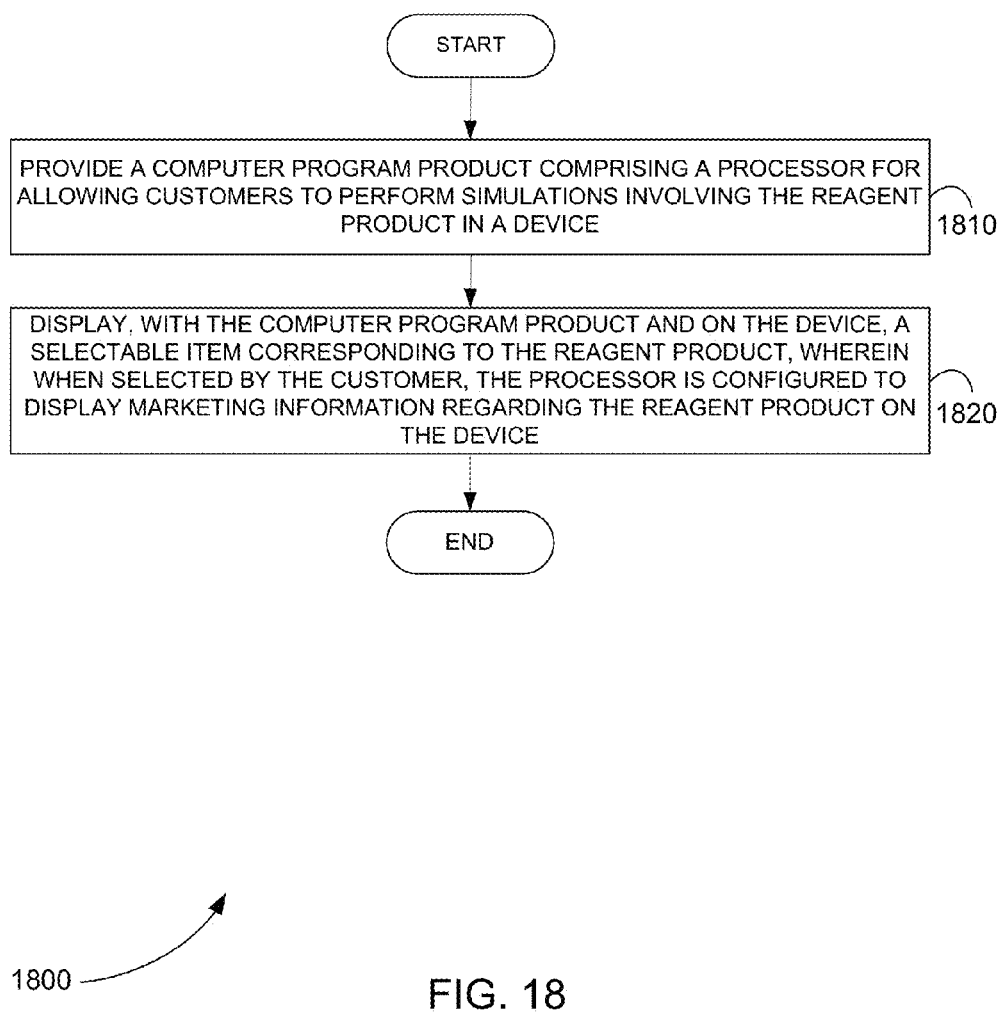
FIG. 18 is an exemplary flowchart showing a method for obtaining information about a reagent product used in a simulated environment.

FIG. 18 is an exemplary flowchart showing a method 1800 for obtaining information about a reagent product used in a simulated environment.

In step 1810 of method 1800, a computer program product including a processor can be provided for allowing customers to perform simulations involving the reagent product in a device.

In step 1820, a selectable item corresponding to the reagent product can be displayed using the computer program product and on the device. When selected by the customer, the processor can be configured to display marketing information regarding the reagent product on the device.

The computer program product can include a mobile phone device or a laboratory instrument, for example. In various embodiments, the computer program product can be one or more of a computer, a tablet device, a gaming device, a music player, and a video player.

Figure 19:
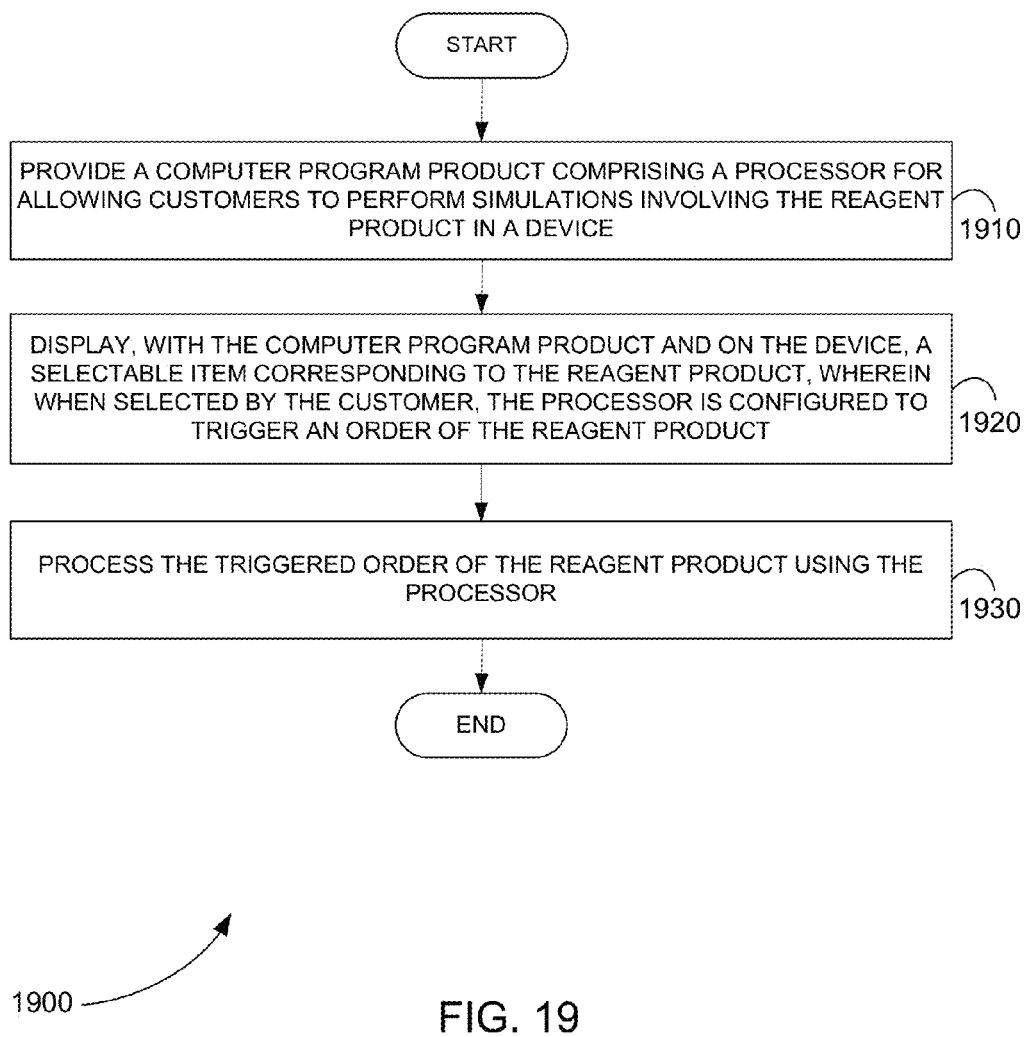
FIG. 19 is an exemplary flowchart showing a method for allowing a customer to order a reagent product.

FIG. 19 is an exemplary flowchart showing a method 1900 for allowing a customer to order a reagent product.

In step 1910 of method 1900, a computer program product including a processor can be provided for allowing customers to perform simulations involving the reagent product in a device.

In step 1920, a selectable item corresponding to the reagent product can be displayed using with the computer program product and on the device. When selected by the customer, the processor can be configured to trigger an order of the reagent product.

In step 1930, the triggered order of the reagent product can be processed using the processor.

Reagent Product Selection Systems, Methods, and Computer Program Products

According to an exemplary embodiment, provided herein is a system for displaying one or more reagent products to potential customers, including (1) a memory that can store information about a plurality of reagent products categorized among a plurality of reagent product categories, including identification information and one or more characteristics for each of the reagent products; (2) an input device; (3) a display; and (4) a processor in communication with the memory, the input device, and the display, the processor being configured to (a) receive a reagent product category selected from the reagent product categories using the input device; (b) retrieve one or more reagent products corresponding to the received reagent product category from the memory; (c) display the retrieved one or more reagent products on the display, including displaying the identification information and at least one of the one or more characteristics of the retrieved one or more reagent products; (d) receive a reagent product selected from the displayed one or more reagent products using the input device; (e) display, upon user selection of a reagent product information icon, an information view screen including the one or more characteristics of the received reagent product; and (f) display, upon user selection of a reagent product protocol icon, a protocol view screen including one or more steps of an experimental protocol for using the received reagent product.

In this system, the reagent product categories can include, but is not limited to: one or more of a GFP category, a cell tracking category, an antifades category, a cytoskeleton category, a trafficking category, an antibody labeling category, an organelle stains category, an apoptosis category, a cell cycle category, a cell viability category, an oxidative stress category, a cell proliferation category, an immunofluorescence category, an autophagy category, a DNA stains category, an epitope tags category, an RNA biology category, an ion indicators category, an essentials category, and a protein labeling category. The processor can further be configured to display (when displaying the retrieved one or more reagent products on the display) one or more characteristics of each of the retrieved one or more reagent products, including a graphical dial illustrating a hands-on time or a total time needed to perform an experimental protocol corresponding to each of the retrieved one or more reagent products. The processor can further be configured to display (when displaying the retrieved one or more reagent products on the display) one or more characteristics of each of the retrieved one or more reagent products, including an indication as to whether each of the retrieved one or more reagent products is a live cell product or a product that has been fixed by chemical treatment. The input device can include a touch screen of the display. The processor can further be configured to display the retrieved one or more reagent products on the display as one or more selectable items that when selected provides more information on the selected item, and can further be configured to display a selectable icon on the display that when selected begins a process of ordering the selected item. The system can be one or more of a computer, a mobile phone, a tablet device, a gaming device, a music player, a video player, and a laboratory instrument.

According to another exemplary embodiment, provided herein is a method for displaying information and experimental protocols about reagent products, including: (1) storing a plurality of reagent products categorized among a plurality of reagent product categories, including identification information and one or more characteristics for each of the reagent products, using a memory; (2) receiving a reagent product category selected from the reagent product categories using a processor; (3) retrieving one or more reagent products corresponding to the received reagent product category from the memory using the processor; (4) displaying the retrieved one or more reagent products on a display, including displaying the identification information and at least one of the one or more characteristics of the retrieved one or more reagent products, on the display using the processor; (5) receiving a reagent product selected from the displayed one or more reagent products using the processor; (6) displaying, upon user selection of a reagent product information icon, an information view screen including the one or more characteristics of the received reagent product; and (7) displaying, upon user selection of a reagent product protocol icon, a protocol view screen including one or more steps of an experimental protocol for using the received reagent product.

In this method, storing a plurality of reagent products categorized among a plurality of reagent product categories can further include, but is not limited to, categorizing the reagent products among one or more of a GFP category, a cell tracking category, an antifades category, a cytoskeleton category, a trafficking category, an antibody labeling category, an organelle stains category, an apoptosis category, a cell cycle category, a cell viability category, an oxidative stress category, a cell proliferation category, an immunofluorescence category, an autophagy category, a DNA stains category, an epitope tags category, an RNA biology category, an ion indicators category, an essentials category, and a protein labeling category. Further, receiving a reagent product category selected from the reagent product categories can further include receiving a reagent product category from a touch screen of the display. The method can further include displaying the reagent product selected from the displayed one or more reagent products as a selectable item that when selected provides more information on the selected reagent product, and it can further include displaying a selectable icon on the display that when selected begins a process of ordering the reagent product selected from the displayed one or more reagent products.

According to another exemplary embodiment, provided herein is a computer program product, including a non-transitory and tangible computer-readable storage medium whose contents can include a program with instructions being executed on a processor so as to perform a method for displaying information and experimental protocols about reagent products, the method including: (1) providing a system, wherein the system includes one or more distinct software modules, and wherein the distinct software modules include a storage module and a display module; (2) storing a plurality of reagent products categorized among a plurality of reagent product categories, including identification information and one or more characteristics for each of the reagent products, using a memory; (3) receiving a reagent product category selected from the reagent product categories using a processor; (4) retrieving one or more reagent products corresponding to the received reagent product category from the memory using the processor; (5) displaying the retrieved one or more reagent products on a display, including displaying the identification information and at least one of the one or more characteristics of the retrieved one or more reagent products, on the display using the processor; (6) receiving a reagent product selected from the displayed one or more reagent products using the processor; (7) displaying, upon user selection of a reagent product information icon, an information view screen including the one or more characteristics of the received reagent product; and (8) displaying, upon user selection of a reagent product protocol icon, a protocol view screen including one or more steps of an experimental protocol for using the received reagent product.

In this computer program product, storing a plurality of reagent products categorized among a plurality of reagent product categories can further include, but is not limited to, categorizing the reagent products among one or more of a GFP category, a cell tracking category, an antifades category, a cytoskeleton category, a trafficking category, an antibody labeling category, an organelle stains category, an apoptosis category, a cell cycle category, a cell viability category, an oxidative stress category, a cell proliferation category, an immunofluorescence category, an autophagy category, a DNA stains category, an epitope tags category, an RNA biology category, an ion indicators category, an essentials category, and a protein labeling category. The reagent product category and the selected reagent product can be received using a touch screen of the display. The method performed by the instructions can further include displaying the reagent product selected from the displayed one or more reagent products as a selectable item that when selected provides more information on the selected reagent product. The method performed by the instructions can further include displaying a selectable icon on the display that when selected begins a process of ordering the reagent product selected from the displayed one or more reagent products.

According to another exemplary embodiment, provided herein is a method for listing reagent products, including: (1) storing information about a plurality of reagent products and corresponding composition information and experimental protocol information using a memory in a device; (2) displaying, in a first view screen on a display of the device, one or more subsets of the plurality of reagent products together with summary information describing the displayed reagents products and an experimental protocol corresponding to the displayed reagents products; and (3) displaying, in a second view screen of the display corresponding to a user selected reagent product and upon further selection by a user of an information icon, detailed information about one or more of an amount, a concentration, a molecular weight, and storage conditions of each constituents of the user selected reagent product.

This method can further include displaying, in a third view screen corresponding to a user selected reagent product and upon selection by a user of a protocol icon, detailed information about one or more steps of an experimental protocol for using the user selected reagent product, the one or more steps including one or more of a removing step, a washing step, a making step, a diluting step, a pre-mixing step, a centrifuging step, a transferring step, a stirring step, an adding step, an incubating step, and an imaging step. In this method, the device can be a mobile phone device, or it can be a laboratory instrument, or it can be one or more of a computer, a tablet device, a gaming device, a music player, and a video player, for example.

According to another exemplary embodiment, provided herein is a method for allowing a customer to order a reagent product, including: (1) providing a computer program product including a processor for allowing customers to obtain information about one or more reagent products using a device; (2) displaying, in a first view screen of a display on the device, one or more subsets of the plurality of reagent products together with information describing the displayed reagents products and one or more experimental protocols corresponding to the displayed reagents products; (3) displaying, in a second view screen of the display corresponding to a user selected reagent product and upon further selection by a user of an information icon, detailed information about one or more of an amount, a concentration, a molecular weight, and storage conditions of each constituents of the user selected reagent product; (4) displaying, in a third view screen of the display corresponding to a user selected reagent product and upon further selection by a user of an protocol icon, detailed information about one or more steps of an experimental protocol for using the user selected reagent product, the one or more steps including one or more of a removing step, a washing step, a making step, a diluting step, a pre-mixing step, a centrifuging step, a transferring step, a stirring step, an adding step, an incubating step, and an imaging step; (5) displaying, with the computer program product and on the display, a selectable item corresponding to the user selected reagent product, wherein when selected by the customer, the processor is configured to trigger an order of the reagent product; and (6) processing the triggered order of the reagent product using the processor.

In this method, the device can be a mobile phone device, or a laboratory instrument, or one or more of a computer, a tablet device, a gaming device, a music player, and a video player, for example.

As described above, the computer program product can include a mobile phone device or a laboratory instrument, for example. In various embodiments, the computer program product can be one or more of a computer, a tablet device, a gaming device, a music player, and a video player.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

It should also be understood that the embodiments described herein can employ various computer-implemented operations involving data stored in computer systems. These operations are those requiring physical manipulation of physical quantities. Usually, though not necessarily, these quantities take the form of electrical or magnetic signals capable of being stored, transferred, combined, compared, and otherwise manipulated. Further, the manipulations performed are often referred to in terms, such as producing, identifying, determining, or comparing.

Any of the operations that form part of the embodiments described herein are useful machine operations. The embodiments, described herein, also relate to a device or an apparatus for performing these operations. The systems and methods described herein can be specially constructed for the required purposes or it may be a general purpose computer selectively activated or configured by a computer program stored in the computer. In particular, various general purpose machines may be used with computer programs written in accordance with the teachings herein, or it may be more convenient to construct a more specialized apparatus to perform the required operations.

What is claimed is:

1. A system for displaying one or more artificially rendered cell structures of a biological cell, comprising:
   a memory configured to store a plurality of virtual cell structures of a biological cell and one or more virtual stain colors for each cell structure;
   an input device;
   a display; and
   a processor in communication with the memory, the input device, and the display, the processor configured to:
      receive a first and a second selected cell structure from the input device, wherein the second selected cell structure is not the same cell structure as the first selected cell structure;
      retrieve one or more stain colors for each of the first and the second selected cell structures from the memory;
      display the one or more stain colors for each of the first and the second selected cell structures on the display;
      receive a first and a second selected stain color from the input device; and
      display the first selected cell structure in the first selected stain color and the second selected cell structure in the second selected stain color in an exemplary artificially rendered cell image on the display that is representative of a staining of the first and the second selected cell structures in the first and the second selected stain colors wherein the exemplary artificially rendered cell image on the display comprises a crosstalk between the first selected stain color and the second selected stain color.

2. The system of claim 1, wherein the memory is further configured to store one or more reagent products that can produce each stain color, and wherein the processor is further configured to retrieve one or more reagent products of the first and the second selected stain colors from the memory, display the one or more reagent products of the first and the second selected stain colors on the display, receive a selected reagent product from the input device, and display the selected reagent product on the display.

3. The system of claim 2, wherein the processor is further configured to display the selected reagent product on the display as a selectable item that when selected provides more information on the selected reagent product.

4. The system of claim 2, wherein the processor is further configured to display a selectable item on the display that when selected begins a process of ordering the selected reagent product.

5. The system of claim 1, wherein the plurality of virtual cell structures are stored as images.

6. The system of claim 5, wherein the images are three-dimensional.

7. The system of claim 1, wherein the exemplary artificially rendered cell image is a compilation of two or more cell images.

8. A method for displaying artificially rendered cell structures of a biological cell, comprising:
   storing a plurality of virtual cell structures of a biological cell and one or more virtual stain colors for each cell structure using a memory;
   receiving a first and a second selected cell structure from an input device using a processor, wherein the second selected cell structure is not the same as the first selected cell structure;

retrieving one or more stain colors for each of the first and the second selected cell structure from the memory using the processor;

displaying the one or more stain colors for each of the first and the second selected cell structure on a display using the processor;

receiving a first and a second selected stain color from the input device using the processor; and displaying the first selected cell structure in the first selected stain color and the second selected cell structure in the second selected stain color in an exemplary artificially rendered cell image on the display that is representative of a staining of the first and the second selected cell structures in the first and second selected stain colors using the processor wherein the exemplary artificially rendered cell image on the display comprises a crosstalk between the first selected stain color and the second selected stain color using the processor.

9. The method of claim 8, further comprising storing one or more reagent products that can produce each stain color, retrieving one or more reagent products of the first and second selected stain colors from the memory using the processor, displaying the one or more reagent products of the first and second selected stain colors on the display using the processor, receiving a selected reagent product from the input device using the processor, and displaying the selected reagent product on the display using the processor.

10. The method of claim 9, further comprising displaying the selected reagent product on the display as a selectable item that when selected provides more information on the selected reagent product using the processor.

11. The method of claim 9, further comprising displaying a selectable item on the display that when selected begins a process of ordering the selected reagent product using the processor.

12. The method of claim 8, wherein the plurality of virtual cell structures are stored as images.

13. The method of claim 12, wherein the images are three-dimensional.

14. The method of claim 8, wherein displaying the first and second selected cell structures in the first and second selected stain colors in the exemplary artificially rendered cell image further comprises displaying the first and second selected cell structures as a compilation of two or more cell images.

15. A computer program product, comprising a non-transitory and tangible computer-readable storage medium whose contents include a program with instructions being executed on a processor so as to perform a method for displaying artificially rendered cell structures of a biological cell, the method comprising:

providing a system, wherein the system comprises one or more distinct software modules, and wherein the distinct software modules comprise a storage module and a stain module;

storing a plurality of virtual cell structures of a biological cell and one or more virtual stain colors for each cell structure in a memory using the storage module;

receiving a first and a second selected cell structure from an input device using the stain module;

retrieving one or more stain colors for each of the first and the second selected cell structures from the memory using the storage module;

displaying the one or more stain colors for each of the first and the second selected cell structures on a display using the stain module;

receiving a first and a second selected stain color from the input device using the stain module; and displaying the first selected cell structure in the first selected stain color and the second selected cell structure in the second selected stain color in an exemplary artificially rendered cell image on the display that is representative of a staining of the first and second selected cell structures in the selected stain color using the stain module wherein the exemplary artificially rendered cell image on the display comprises a crosstalk between the selected stain color and the second selected stain color using the stain module.

16. The computer program product of claim 15, wherein the method performed by the instructions further comprises storing one or more reagent products that can produce each stain color using the storage module, retrieving one or more reagent products of the first and the second selected stain colors from the memory using the storage module, displaying the one or more reagent products of the first and the second selected stain colors on the display using the stain module, receiving a selected reagent product from the input device using the stain module, and displaying the selected reagent product on the display using the stain module.

17. The computer program product of claim 16, wherein the method performed by the instructions further comprises displaying the selected reagent product on the display as a selectable item that when selected provides more information on the selected reagent product using the stain module.

18. The computer program product of claim 16, wherein the method performed by the instructions further comprises displaying a selectable item on the display that when selected begins a process of ordering the selected reagent product using the stain module.

19. The computer program product of claim 15, wherein the plurality of virtual cell structures are stored as images.

20. The computer program product of claim 19, wherein the images are three-dimensional images.

21. The computer program product of claim 15, wherein the exemplary artificially rendered cell image is a compilation of two or more cell images.

22. A system for displaying one or more artificially rendered cell structures of a biological cell, comprising:

a memory configured to store a plurality of virtual cell structures of a biological cell and one or more virtual stain colors for each cell structure; and a processor in communication with the memory and an input device, the processor further configured to:

receive a first and a second selected cell structure from the input device;

retrieve one or more stain colors for each of the first and the second selected cell structures from the memory;

communicate and display the one or more stain colors for each of the first and the second selected cell structures on the input device;

receive a first and a second selected stain color from the input device; and communicate and display the first selected cell structure in the first selected stain color and the second selected cell structure in the second selected stain color in an exemplary artificially rendered cell image on the input device that is representative of a staining of the first and the second selected cell structures in the first and the second selected stain colors wherein the exemplary artificially rendered cell image on the display artificially rendered crosstalk between the selected stain color and the second selected stain color using the stain module.

23. The system of claim 22, wherein the processor communicates with the input device via a network connection.

24. The system of claim 23, wherein the first and the second selected cell structures and first and the second selected stain colors are displayed on a web browser running on the input device.

* * * * *